United States Patent
Wellington et al.

(10) Patent No.: US 10,451,637 B2
(45) Date of Patent: Oct. 22, 2019

(54) SYNTHETIC BLOOD VESSELS AND USES THEREOF

(71) Applicant: THE UNIVERSITY OF BRITISH COLUMBIA, Vancouver, BC (CA)

(72) Inventors: Cheryl Wellington, Vancouver (CA); Jerome Robert, Vancouver (CA)

(73) Assignee: THE UNIVERSITY OF BRITISH COLUMBIA, Vancouver, BC (CA)

( * ) Notice: Subject to any disclaimer, the term of this patent is extended or adjusted under 35 U.S.C. 154(b) by 0 days.

(21) Appl. No.: 15/935,820

(22) Filed: Mar. 26, 2018

(65) Prior Publication Data

US 2018/0275147 A1    Sep. 27, 2018

Related U.S. Application Data

(60) Provisional application No. 62/476,191, filed on Mar. 24, 2017.

(51) Int. Cl.
  *G01N 33/68* (2006.01)
  *G01N 33/50* (2006.01)

(52) U.S. Cl.
  CPC ..... *G01N 33/6896* (2013.01); *G01N 33/5058* (2013.01); *G01N 33/5061* (2013.01); *G01N 33/5064* (2013.01); *G01N 33/5082* (2013.01); *G01N 2333/4709* (2013.01); *G01N 2800/2821* (2013.01); *G01N 2800/2871* (2013.01); *G01N 2800/50* (2013.01)

(58) Field of Classification Search
  None
  See application file for complete search history.

(56) References Cited

U.S. PATENT DOCUMENTS

| | | | |
|---|---|---|---|
| 5,591,225 A * | 1/1997 | Okuda | A61L 27/34 623/1.39 |
| 6,537,567 B1 | 3/2003 | Niklason et al. | |
| 2006/0085063 A1 | 4/2006 | Shastri et al. | |
| 2006/0240061 A1 | 10/2006 | Atala et al. | |

OTHER PUBLICATIONS

Snyder, 2015, Alzheimer's & Dementia, 11, 710-717 (Year: 2015).*
Argyri, L. et al., "Molecular Basis for Increased Risk for Late-onset Alzheimer Disease Due to the Naturally Occurring L28P Mutation in Apolipoprotein E4*", J Biol Chem. May 2, 2014;289(18):12931-45.
Attems and Jellinger, "The overlap between vascular disease and Alzheimer's disease—lessons from pathology", 2014 BMC Med 12(206).
Choi et al., "A three-dimensional human neural cell culture model of Alzheimer's disease", 2014, Nature 515: 274-278.
Cucullo et al., "Development of a Humanized In Vitro Blood—Brain Barrier Model to Screen for Brain Penetration of Antiepileptic Drugs", 2007, Epilepsia 48(3):505-516.
Duron and Hanon, "Vascular risk factors, cognitve decline, and dementia", 2008 Vasc Health Risk Manag 4(2):363-81.
Fan et al. "Identification of a Chrysanthemic Ester as an Apolipoprotein E Inducer in Astrocytes", 2016 PLoS One. Sep. 6;11(9):e0162384.
Getz and Reardon, "Animal Models of Atherosclerosis", 2012 Arterioscler Thromb Vasc Biol 32(5):1104-15.
Giri et al., "Genes associated with Alzheimer's disease: an overview and current status", 2016 Clin Intery Aging 11:665-681.
Hye et al., "Plasma proteins predict conversion to dementia from prodromal disease", 2014, Alzheimers Dement 10 (6):799-807.
Mayeaux and Stern, "Epidemiology of Alzheimer Disease", 2012 CSH Perspect Med 2(8).
Merched et al., "Decreased high-density lipoprotein cholesterol and serum apolipoprotein Al concentrations are highly correlated with the severity of Alzheimer's disease", 2000, Neurobiol Aging 21(1):27-30.
Reitz et al., "Association of Higher Levels of High-Density Lipoprotein Cholesterol in Elderly Individuals and Lower Risk of Late-Onset Alzheimer Disease", 2010 Arch Neurol 67(12):1491-7.
Robert et al., "Interleukin 6 Stimulates Endothelial Binding and Transport of High-Density Lipoprotein Through Induction of Endothelial Lipase", 2013, Arterioscler Thromb Vasc 33(12):2699-70624115033.
Sacre et al., "Apolipoprotein E (apoE) isoforms differentially induce nitric oxide production in endothelial cells", 2003 FEBS Lett 540:181-187.
Shih et al., "Apolipoprotein C-III is an Amyloid-β-Binding Protein and an Early Marker for Alzheimer's Disease", 2014 J Alzheimers Dis 41(3):855-65.
Snyder et al., "Vascular contributions to cognitive impairment and dementia including Alzheimer's disease", 2015, Alzheimers Dement 11(6):710-7.
Stukas et al., "High-Density Lipoproteins and Cerebrovascular Integrity in Alzheimer's Disease", 2014, Cell Metab 19 (4):574-91.
Ueno et al., "Clearance of Beta-Amyloid in the Brain", 2014, Curr Med Chem 21(35):4085-90.
Zlokovic, "Cerebrovascular Effects of Apolipoprotein E", 2013, JAMA Neurol 70(4):440-444.
Zuliani et al., "Relationship Between Low Levels of High-Density Lipoprotein Cholesterol and Dementia in the Elderly. The InChianti Study", 2010 J Gerontol A Biol Sci Med Sci 65A(5):559-56.

* cited by examiner

*Primary Examiner* — Satyanarayana R Gudibande

(57) ABSTRACT

The present invention provides a synthetic blood vessel and use thereof in drug screening, drug delivery and prognoses of cerebrovascular dysfunction.

7 Claims, 26 Drawing Sheets

Specification includes a Sequence Listing.

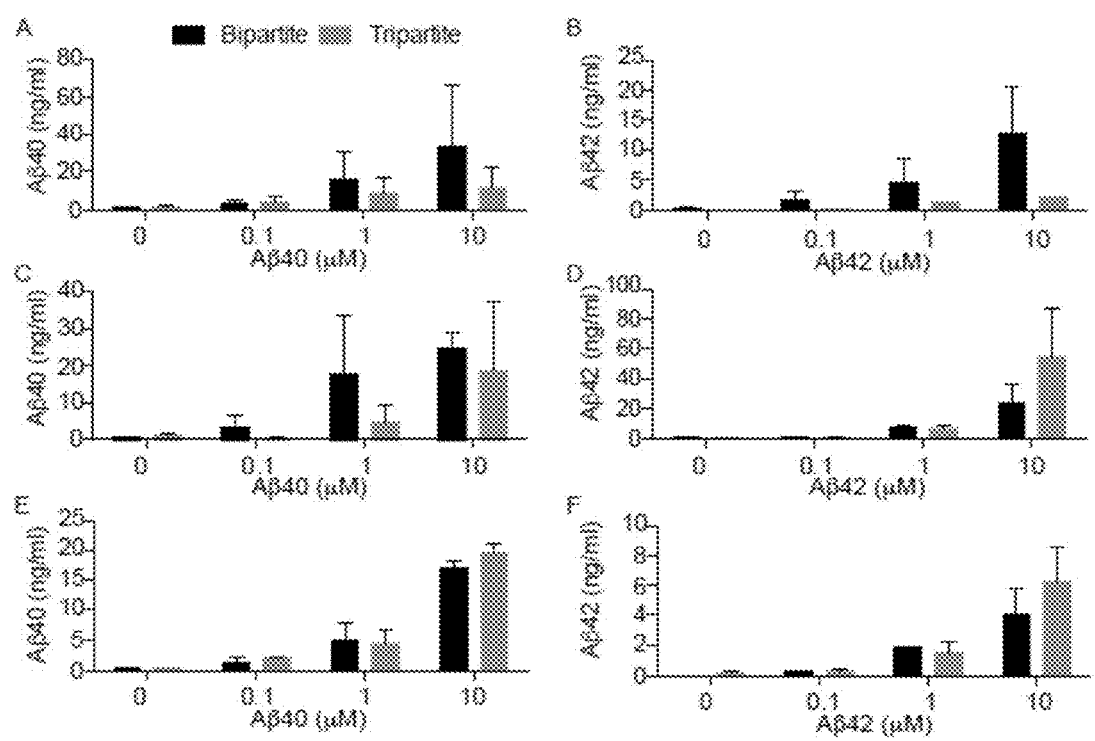
FIGURE 6A-F

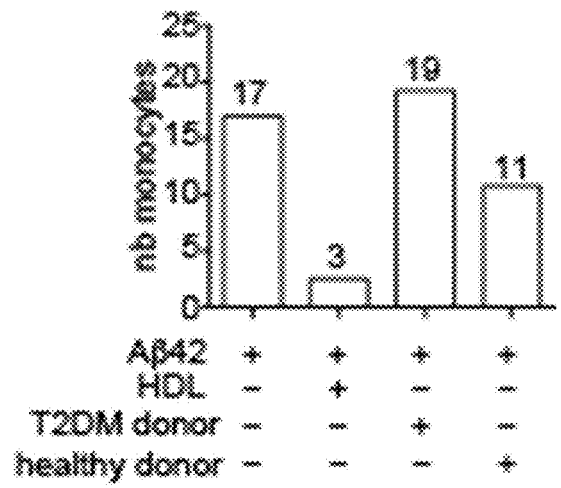
FIGURE 8C
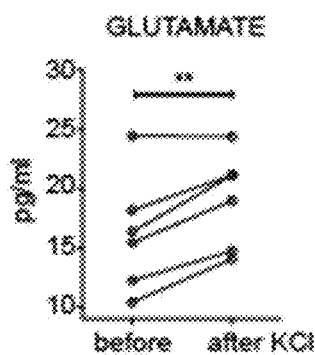
FIGURE 9A
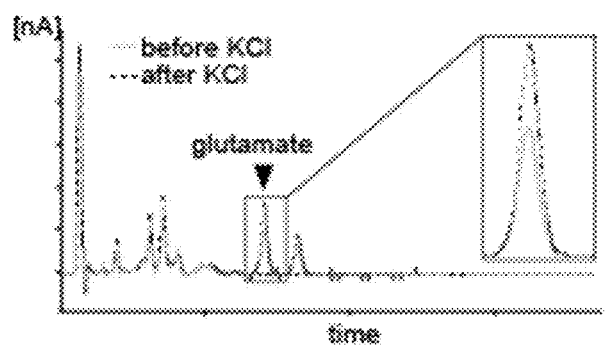

```
SEQUENCE LISTING

<160> NUMBER OF SEQ ID NOS: 2

<210> SEQ ID NO 1
<211> LENGTH: 40
<212> TYPE: PRT
<213> ORGANISM: Homo sapiens

<400> SEQUENCE: 1

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val
        35                  40

<210> SEQ ID NO 2
<211> LENGTH: 42
<212> TYPE: PRT
<213> ORGANISM: Homo sapiens
```

```
<400> SEQUENCE: 2

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
            35                  40
```

SYNTHETIC BLOOD VESSELS AND USES THEREOF

CROSS REFERENCE TO RELATED APPLICATIONS

This application claims the benefit of priority of U.S. Provisional Patent Application No. 62/476,191, filed Mar. 24, 2017, which is incorporated herein by reference in its entirety.

FIELD OF INVENTION

The present invention relates to synthetic blood vessels and uses thereof. More specifically, the present invention relates to synthetic blood vessels for use in drug screening, drug delivery or prognoses of cerebrovascular dysfunction.

BACKGROUND OF THE INVENTION

Alzheimer's Disease (AD) is a leading cause of senile dementia with over 44 million affected persons and an economic burden of over $600 billion (Mayeaux and Stern, 2012 CSH Perspect Med 2(8)). Neuropathological hallmarks of AD include amyloid plaques containing deposited Aβ peptides, neurofibrillary tangles containing hyperphosphorylated tau proteins, and in 60-90% of cases, cerebral vessel disease, including cerebral amyloid angiopathy (CAA), small vessel disease, and microvascular degeneration (Attems and Jellinger, 2014 BMC Med 12(206)).

Apolipoprotein (apo)E, which is primarily secreted in the brain from astrocytes, and also from microglia and pericytes, has been hypothesized to contribute to cerebrovascular dysfunction (Zlokovic, 2013 JAMA Neurol 70(4):440-444) and also is the principal lipid carrier within the brain, having a role in lipid metabolism (Gin et al., 2016 Clin Intery Aging 11:665-681). ApoE has been implicated in Aβ metabolism with apoE4 being detrimental, apoE3 neutral and apoE2 protective. The major routes by which Aβ is cleared from the brain involve the cerebrovasculature (Ueno et al., 2014 Curr Med Chem 21(35):4085-90), with implications for dementia (Snyder et al., 2015 Alzheimers Dement 11(6):710-7).

Cardiovascular risk factors, including type 2 diabetes mellitus (T2DM), hypertension, hypercholesterolemia, obesity and stroke increase AD risk (Duron and Hanon, 2008 Vasc Health Risk Manag 4(2):363-81). Epidemiological studies suggest that risk of AD may be attenuated by high levels of circulating high-density lipoprotein cholesterol (HDL-C), which has been associated with reduced cardiovascular disease (CVD) risk (Zuliani et al., 2010 J Gerontol A Biol Sci Med Sci 65A(5):559-564). Specifically, levels of apoA-I, the major HDL-associated protein, have been shown to positively correlate with Mini-Mental State Examination (MMSE) and Cognitive Ability Screening Instrument (CASI) scores (Shih et al., 2014 J Alzheimers Dis 41(3): 855-65; Merched et al., 2000 Neurobiol Aging 21(1):27-30) and high serum HDL-cholesterol (HDL-C) levels (>55 mg/dL) in cognitively normal elderly individuals are associated with significantly reduced risk (HR 0.4) of AD, even after adjusting for APOE genotype and vascular risk factors including obesity and T2DM (Reitz et al., 2010 Arch Neurol 67(12):1491-7). In symptomatic AD patients, plasma apoA-I levels negatively correlate with hippocampal and whole brain volume as well as mean entorhinal cortical thickness (Hye et al., 2014 Alzheimers Dement 10(6):799-807), and decreased levels of serum apoA-I can discriminate AD from non-demented age-matched control subjects (Shih et al., 2014 J Alzheimers Dis 41(3):855-65). HDL and apoE have several potent vasoprotective functions including reducing inflammation, increasing vascular tone through promoting endothelial nitric oxide (NO) synthase activity, and suppressing vascular adhesion molecule expression (Stukas et al., 2014 Cell Metab 19(4):574-91; Sacre et al., 2003 FEBS Lett 540:181-187).

Animal models, such as mice genetically engineered to express human amyloid precursor protein (APP), which enables the study of progressive accumulation of Aβ and β-amyloid, have been used to study Aβ egress through cerebral vessels. There are however innate physiological differences between murine and human lipoprotein metabolism (Getz and Reardon, 2012 Arterioscler Thromb Vasc Biol 32(5):1104-15). For example, the primary circulating lipoprotein in rodents is HDL, which, due to its multiple vasoprotective functions, bestows upon mice a natural resilience to cardiovascular diseases such as atherosclerosis. By contrast, the major circulating lipoprotein in humans is low-density lipoprotein (LDL), which is mechanistically linked to vascular dysfunction and cardiovascular disease.

In vitro studies using human cells represents an alternative approach, however, most studies of the blood brain barrier (BBB) use monotypic cultures of brain endothelial cells (ECs), which do not mimic the complexity of cell-cell and/or cell-matrix interactions found in the native vessel. ECs and astrocytes, EC and smooth muscle cells (SMC) or EC and pericytes have been co-cultured, yet this is typically done under static culture conditions. A more recent study described an EC and astrocyte co-culture model using a complex flow system, but this model did not allow histology analysis or cell-extracellular matrix (ECM) interactions to be assessed (Cucullo et al., 2007 Epilepsia 48(3):505-516). A recent study using human induced pluripotent stem cells (IPSC)-derived neurons have demonstrated the formation on complex neurological organoids, but this model lacks the vasculature (Choi et al., 2014 Nature 515: 274-278.)

SUMMARY OF THE INVENTION

The present invention provides, in part, a synthetic blood vessel and use thereof in drug screening, drug delivery and prognoses of cerebrovascular dysfunction.

In one aspect, the invention provides a method of identifying an amyloid beta (Aβ) modulator by: providing a synthetic blood vessel, providing an Aβ peptide; providing a test compound; contacting the synthetic blood vessel with the Aβ peptide; contacting the synthetic blood vessel with the test compound; and determining the level of Aβ deposition or transport, where the test compound is an Aβ modulator if it inhibits Aβ deposition or enhances Aβ transport.

In some embodiments, the method may further include contacting the synthetic blood vessel with a lipoprotein, such an apolipoprotein or a high-density lipoprotein (HDL). In some embodiments, the apolipoprotein may be an apoE isoform. In some embodiments, the lipoprotein may be from an astrocyte, unfractionated plasma or serum.

In some embodiments, the Aβ peptide may be an Aβ40 peptide or an Aβ42 peptide. In some embodiments, the Aβ peptide may be from a neuronal cell.

In some embodiments, the test compound may be added prior to the addition of the Aβ peptide; simultaneously with the Aβ peptide; or subsequent to the addition of the Aβ peptide.

In some embodiments, the synthetic blood vessel may be a bipartite vessel, a tripartite vessel, a quadripartite vessel or a pentapartite vessel.

In some embodiments, the synthetic blood vessel may be coupled to a Fluid flow system.

In some embodiments, the determining may be done by an immunological assay or a microscopy assay.

In some aspects, the present invention provides a method of determining the risk for a cerebrovascular dysfunction in a subject in need thereof by: providing a synthetic blood vessel; providing an Aβ peptide; contacting the synthetic blood vessel with a sample from the subject; and determining the level of Aβ deposition or transport in the sample, where the subject has an increased risk for a cerebrovascular dysfunction if the level of Aβ deposition is increased or if Aβ transport is reduced.

In some embodiments, the method further includes monitoring the risk for the cerebrovascular dysfunction.

In some embodiments, the sample comprises HDL or apoE or a combination thereof.

In some embodiments, the method further includes providing a monocyte cell and determining the level of monocyte adhesion.

In some embodiments, the method further includes determining the level of endothelial cell activation.

In some embodiments, the cerebrovascular dysfunction may be type II diabetes mellitus (T2DM), hypercholesterolemia, hypertension, cerebral amyloid angiopathy (CAA), ischemic brain injury, stroke, dementia, cognitive impairment or Alzheimer's disease.

In some embodiments, the subject may be a human.

In some aspects, the present invention provides a method of determining whether a compound is suitable for delivery to the brain, by: providing a synthetic blood vessel, wherein the synthetic blood vessel is at least a tripartite vessel; contacting the lumen of the synthetic blood vessel with a test compound; determining the level of transport of the test compound to the antelumen of the tripartite vessel, where the test compound is suitable for delivery to the brain if it is transported to the antelumen of the tripartite vessel.

In some aspects, the present invention provides a synthetic blood vessel kit including a synthetic blood vessel and an amyloid beta (Aβ) peptide, together with instructions for use, where the synthetic blood vessel kit optionally further includes a lipoprotein or a monocytic cell or a combination thereof.

This summary of the invention does not necessarily describe all features of the invention.

BRIEF DESCRIPTION OF THE DRAWINGS

These and other features of the invention will become more apparent from the following description in which reference is made to the appended drawings wherein:

FIG. 6A is a bar graph showing the accumulation of Aβ40 monomers in bipartite and tripartite vessels.

FIG. 6B is a bar graph showing the accumulation of Aβ42 monomers in bipartite and tripartite vessels.

FIG. 6C is a bar graph showing the accumulation of Aβ40 oligomers in bipartite and tripartite vessels.

FIG. 6D is a bar graph showing the accumulation of Aβ42 oligomers in bipartite and tripartite vessels.

FIG. 6E is a bar graph showing the accumulation of Aβ40 fibrils in bipartite and tripartite vessels.

FIG. 6F is a bar graph showing the accumulation of Aβ42 fibrils in bipartite and tripartite vessels.

FIG. 8C is a bar graph showing the number of fluorescently monocytes (THP1) binding to the vessel, where HDL from a healthy donor, or plasma from a type II diabetes mellitus donor, or plasma from a healthy donor has been circulated through the vessel lumen.

FIG. 9A is a scatter plot showing (left panel) and photograph (right panel) the levels of glutamate as measured by HPLC in quadripartite tissues.

DETAILED DESCRIPTION

Figure 1A:
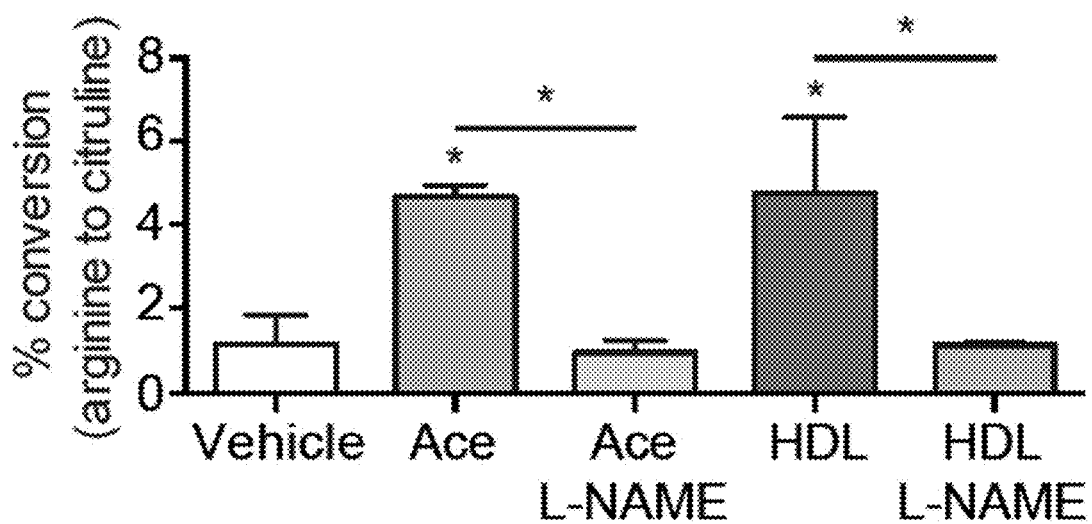
FIG. 1A is a bar graph showing EC function, as confirmed by measuring NO secretion after either acetylcholine (Ach) or HDL stimulation, in the absence or presence of 1 mM of the eNOS inhibitor L-NAME. The graph represents mean±SEM for at least 4 independent experiments. * p=0.05, ** p=0.01 and *' p=0.001.

The present disclosure provides, in part, synthetic blood vessels and uses thereof. In some embodiments, the present disclosure provides a synthetic blood vessel for use as in vitro model for, for example, cerebral amyloid angiopathy (CAA), Alzheimer's disease (AD), or the blood-brain barrier (BBB). In some aspects, the present disclosure provides methods of identifying or screening for compounds that modulate Aβ deposition and clearance. In some aspects, the present disclosure provides methods for monitoring a subject's risk for cerebrovascular dysfunction. In some aspects, the present disclosure provides methods for delivery of a compound for example through the BBB.

By "synthetic blood vessel," as used herein is meant a biologically engineered or "bioengineered" three-dimensional construct including a biocompatible scaffold and at least two types of cells, where the biocompatible scaffold can support the growth and development of the cells. In some embodiments, the synthetic blood vessel may be a cerebrovascular vessel.

The biocompatible scaffold may be made of any suitable material including, but not limited to, a non-woven polyglycolic acid (PGA, Biomedical Structure) mesh (thickness: 0.5-1 mm and density: 70 mg/cc). The biocompatible scaffold may be substantially porous. The biocompatible scaffold may be substantially tubular. In some embodiments, the biocompatible scaffold may be about 0.5 cm to about 10 cm in length, or any value therebetween, such as about 1 cm to about 5 cm, or about 1.5 cm in length. In some embodiments, the inner diameter or the biocompatible scaffold may be about 1 mm to about 6 cm, or any value therebetween, such as between about 2 mm to about 6 mm.

The term "cell," as used herein, may refer to a single cell, a population of cells or one or more layers of cells. In some embodiments, the cells may form distinct layers. In some embodiments, the cell may be for incorporation into the synthetic blood vessel. In alternative embodiments, the cell may be added to, for example by injection, the synthetic blood vessel for use in an assay. In some embodiments, the cell may be in suspension or may be adherent. In some embodiments, the cell may be an adherent cell that has formed a monolayer. In some embodiments, the cell may be a primary cell. In some embodiments, the cell may be a cell line, such as hCMEC/D3 (an EC line) or CTG astrocytoma (an astrocyte line). In some embodiments, the cell may be native (i.e., isolated from an organism, such as a human or animal) or may be cultured in vitro. In some embodiments, the cell may be derived from a progenitor cells or from an induced pluripotent stem cell (iPSC).

In some embodiments, the cells for incorporation into the synthetic blood vessel may include, without limitation, muscular cells, vascular associated fibroblasts, endothelial cells, pericytes, glial cells (including without limitation astrocyte and microglia), or neuronal cells. In some embodiments, the cells for use in, for example, an assay may include without limitation blood cells (including without limitation PMBC, monocytes (such as THP1), lymphocytes, leukocytes, T cells, red blood cells, platelets, cancer cells, bacterial cells, pathogenic cells such as parasitic cells etc. In some embodiments, the cell may be a vascular cell e.g., a cell typically found in or associated with vascular tissue such as, without limitation, an endothelial cell (EC), a smooth muscle cell (SMC), a pericyte, a macrophage, a monocyte, or an astrocyte.

A "muscular cell," as used herein, refers to or describes a contractile cell type that can be used to generate the muscular cell layer of a bioengineered cerebrovascular vessel as described herein. A muscular cell includes, without limitation, a smooth muscle cell (SMC), a myofibroblast, or a pericyte. SMC can be isolated from humans or animals, or can be derived from progenitor cells, or from induced pluripotent stem cells. A SMC can be found in a blood vessel and, through contraction, is capable of regulating blood flow and transport of various substances through a blood vessel. In some embodiments, vascular SMC can form circumferential layers.

The term "EC," as used herein, refers to or describes endothelial cells. EC line the interior surface of blood vessels and lymphatic vessels. EC can be isolated from humans or animals, derived from progenitor cells isolated from for example bone marrow or peripheral blood, or from induced pluripotent stem cells. In some embodiments, a term may refer to a single cell, a population of EC or one layer of EC.

The terms "astrocyte" or "astroglia," as used herein, refer to or describe a star-shaped glial cell found in the brain and spinal cord. Astrocytes can be isolated from humans or animals, or can be derived from progenitor cells, or from induced pluripotent stem cells. In some embodiments, an astrocyte may be an induced pluripotent stem cell that has been differentiated into an astrocyte in vitro.

The term "neuron," as used herein, refers to or describes a neuronal cell found in the brain and spinal cord. In some embodiments, a neuron may be an induced pluripotent stem cell that has been differentiated into a neuron in vitro.

The blood monocyte cells may be a peripheral blood mononuclear cell (PBMC) preparation derived from a subject, specific PBMC fractions (monocytes, neutrophils) or may be other monocytic cell lines such as THP-1 cells. The term "PBMC," as used herein, refers to a peripheral blood mononuclear cell. PBMC are peripheral blood cells having a single round nucleus. PBMC include, for example, lymphocytes (such as T cells, B cells, NK cells), dendritic cells, and monocytes. In some embodiments, a PBMC may refer to a mixed population of cell types or a specific cell type. In some embodiments, a PBMC may be derived from a subject. In some embodiments, a PBMC may be cultured in a laboratory.

In some embodiments, the synthetic blood vessel may be a "bipartite vessel" and may include two types of cells, such as an EC and a muscular cell, such as a SMC. In some embodiments, the EC may form an inner layer and the muscular cell may form an outer layer. In some embodiments, the bipartite vessel may resemble a native peripheral blood vessel.

In some embodiments, the synthetic blood vessel may be a "tripartite vessel" and may include three types of cells, such as an EC, a muscular cell, such as a SMC, and an astrocyte. In some embodiments, the EC may form an inner layer, the muscular cell may form a middle layer, and the astrocyte may form an outer layer. In some embodiments, the tripartite vessel may include an EC lining the lumen (inner layer), several layers of muscular cells, such as SMC, and one or more layers of astrocytes in the antelumen (outer layer). In some embodiments, the tripartite vessel may resemble a native cerebral blood vessel. In some embodiments, the tripartite vessel may resemble a leptomeningeal artery or a penetrating artery. In some embodiments, the tripartite vessel may resemble the blood-brain barrier (BBB). The BBB is a highly selective and semi-permeable membrane that acts as a barrier between the brain and the circulatory system. The BBB includes multiple cell types such as EC, astrocytes, SMC and pericytes. The term may refer to a native BBB or a bioengineered BBB. In some embodiments, the tripartite vessel does not resemble the microvasculature.

In some embodiments, the synthetic blood vessel may be a "quadripartite vessel" and may Include four types of cells, such as those typically found in vascular nervous tissue and the neurovascular unit including, without limitation, an EC, a muscular cell, such as a muscular cell, such as a SMC, an astrocyte and a neuron or microglial cell. In some embodiments, the EC may form an inner layer, the muscular cell may form a second, intermediate layer, the astrocyte may form a third, intermediate layer and the neuron or microglial cell may form an outer layer. In some embodiments, astrocytes and neurons may form mixed layers. In some embodiments, the quadripartite vessel may resemble a native cerebral blood vessel. In some embodiments, the quadripartite vessel may resemble a native cerebral cortical artery or vein. In some embodiments, the quadripartite vessel may resemble the neurovascular unit. In some embodiments, the Aβ peptide may be produced endogenously by the neuronal cell component of a quadripartite vessel; in such cases, additional Aβ peptide need not be added. In alternative embodiments, additional, exogenous Aβ peptide may be added to a quadripartite vessel.

In some embodiments, the synthetic blood vessel may be a "pentapartite vessel" and may include five types of cells, such as those typically found in vascular nervous tissue and the neurovascular unit including, without limitation, an EC, a muscular cell, such as a muscular cell, such as a SMC, an astrocyte, a neuron and a microglial cell. In some embodiments, the EC may form an inner layer, the muscular cell may form a second, intermediate layer, the astrocyte may form a third, intermediate layer and the neuron and microglia may form a fourth outer layer. In some embodiments astrocyte and neuron/microglia may form mixed layers. In some embodiments, the pentapartite vessel may resemble a native cerebral blood vessel. In some embodiments, the pentapartite vessel may resemble the neurovascular unit. In some embodiments, the Aβ peptide may be produced endogenously by the neuronal cell component of a pentapartite vessel; in such cases, additional Aβ peptide need not be added. In alternative embodiments, additional, exogenous Aβ peptide may be added to a pentapartite vessel.

By "neurovascular unit," as used herein, is meant the structure, composition and functional association between neurons and the blood vessel system with which they are associated. The neurovascular unit may include multiple cell types such as EC, astrocytes, muscular cells, pericytes, glial cells and/or neurons.

In some embodiments, a synthetic blood vessel may be coupled to a fluid flow system, such as a dynamic, semi-pulsatile flow bioreactor system to, for example, reproduce physiological flow conditions through the blood vessel lumen. The flow system may include tubing forming the circulation loop, a tissue chamber and a medium container to store media and enable gas exchange. The vascular tissue may be placed between two tight connectors that create a separation between the circulation loop (lumen) and the tissue chamber (antelumen, "brain" side). Circulating flow may be applied using a peristaltic pump (for example, from Perkin Elmer). Flow is essential for creating the physiological conditions that resemble blood perfusion through tissue. Aβ accumulation can be studied under static conditions where flow is halted. Temporary stoppage of flow can be used to create conditions of hypoxia and low glucose that resembles stroke.

A synthetic blood vessel may be fabricated using techniques as described herein or known in the art. In one example, a synthetic blood vessel may be optionally fabricated by dip-coating a biocompatible scaffold with a stabilizing polymer, such as polycaprolactone (PCL), polylactate (PLA), etc, to assist growth of the cell on the biocompatible scaffold.

The biocompatible scaffold may then be shaped into tubes of a suitable diameter using heat at about 50° C. to about 80° C. and externally coated with a concentrated solution of stabilizing polymer as above. The biocompatible scaffold may then be sterilized and stored until seeding for a maximum of 15 days at 4° C. Scaffolds may be shaped individually or a long tube may be cut to the desired lengths.

The biocompatible scaffold can be sequentially seeded with a cell at the appropriate density (for example, about 1 million per cm$^2$ to about 3 million per cm$^2$) under suitable conditions. For example, a cell carrier that "jells," such as fibrin, matrigel, collagen, etc., can be added directly to the biocompatible scaffold and a muscular cell can be seeded on the inner (luminal) surface of the biocompatible scaffold. The biocompatible scaffold seeded with a muscular cell can be incubated under static conditions in growth media in an incubator (for example, 37° C., 5% CO$_2$) for a minimum of 3 days. The biocompatible scaffold can then be exposed to dynamic flow and a suitable nutrient medium appropriate to the muscular cell type may be directed through the lumen of a bioreactor circulation loop to mimic blood flow for a minimum of one week.

The biocompatible scaffold can then be seeded with an EC at the appropriate density (for example, 1 million per cm$^2$) under suitable conditions. The biocompatible scaffold seeded with a muscular cell and an EC can be incubated under static conditions in endothelial growth medium supplemented with, for example, 10% FBS for a minimum of 5 days in a nutrient medium suitable for endothelial cells.

After the static phase, for a bipartite vessel, the vessel may be placed back in the bioreactor for minimum of 10 additional days with the desired rate of flow. In some embodiments, the flow rate may be increased to a final rate of 10 ml/min by the 10th day.

For a tripartite vessel, the biocompatible scaffold may be seeded with an astrocyte after the static phase after EC addition, at the appropriate density (1 million per cm$^2$) under suitable conditions. For example, a cell carrier such as fibrin matrigel, collagen, etc can be added to antelumen side of the biocompatible scaffold prior to seeding with the astrocyte. After a cell carrier jells at room temperature, the biocompatible scaffold seeded with a muscular cell, EC and astrocyte may be placed under the desired flow conditions in a suitable medium in the tissue chamber for a minimum of 10 additional days. In some embodiments, the flow rate may be increased to a final rate of 10 ml/min by the 10th day.

For quadripartite and/or pentapartite vessel, the biocompatible scaffold may be kept for a suitable period of time in a suitable medium under static conditions and then seeded with a neuronal cell (days 50-110) and/or a glial cell on the anteluminal side of the tissue using a suitable cell carrier, such as matrigel, collagen, etc. After a cell carrier jells at room temperature, the resulting quadripartite and/or pentapartite tissue may be placed under the desired flow conditions with a suitable neuron media in the circulation and tissue chamber for about 10-30 additional days. In some embodiments, the flow rate may be increased to a final rate of 10 ml/min by the 10th day.

The synthetic blood vessel may be used in a method of identifying an amyloid beta (Aβ) modulator by contacting the synthetic blood vessel with an Aβ peptide and a test compound and determining the level of Aβ deposition or transport, where the test compound is identified as an Aβ modulator of interest, if it inhibits Aβ deposition or enhances Aβ transport. In some embodiments, where the Aβ peptide is produced by the synthetic blood vessel (such as a synthetic blood vessel including neuronal cells), the synthetic blood vessel may be used to determine the ability of a test compound to reduce Aβ peptide expression by neurons.

In some embodiments, the method may include simultaneous addition of the test compound and Aβ peptide. In alternative embodiments, the test compound may be added to the synthetic blood vessel prior to the addition of the Aβ peptide to, for example, determine the ability of the test compound to prevent Aβ accumulation. In alternative embodiments, the test compound may be added to the synthetic blood vessel after the addition of the Aβ peptide to for example determine the ability of the test compound to disrupt Aβ deposition or stimulate Aβ clearance. The test compound may be added to the antelumen "brain side" of the synthetic blood vessel. The test compound may be added to the circulation loop "blood side" of the vessel.

By "amyloid beta" or "Aβ," as used herein, is meant a family of peptides resulting from proteolytic cleavage of the amyloid precursor protein (APP). In some embodiments, an APP protein may have a sequence as set forth in NCBI Accession No. NP_000475. Aβ can be found in the brain and is a major component of amyloid plaques. In some embodiments, an Aβ peptide may include without limitation recombinant Aβ, synthetic Aβ, naturally occurring Aβ, or Aβ produced in vitro through cleavage of neuronally-expressed amyloid precursor protein (APP). In some embodiments, an Aβ peptide may include without limitation a single Aβ peptide monomer, oligomers of Aβ peptides, aggregates of Aβ peptides, fibrils of Aβ peptides. In some embodiments, an Aβ peptide may include different forms of an Aβ peptide, such as Aβ34, Aβ38 Aβ40 and/or Aβ42, or a combination thereof, in any ratio. In some embodiments, Aβ may refer to other proteolytic products of the Aβ34, Aβ38, Aβ40 and/or Aβ42 peptides. In some embodiments, an Aβ40 peptide may refer to the APP cleavage fragment corresponding to the 40 amino acid fragment:

```
                                      (SEQ ID NO: 1)
DAEFRHDSGYEVHHQKLVFFAEDVGSNKGAIIGLMVGGVV.
``` some embodiments, an Aβ42 peptide may refer to the APP cleavage fragment corresponding to the 42 amino acid fragment:

```
                                      (SEQ ID NO: 2)
DAEFRHDSGYEVHHQKLVFFAEDVGSNKGAIIGLMVGGVVIA.
```

By "Aβ deposition" is meant the accumulation of Aβ in an amyloid plaque, which may be diffuse, compact, or neuritic. Aβ deposition can occur within the lumen of a blood vessel or within the walls of a blood vessel. The blood vessel may be natural or bioengineered (for example, a synthetic blood vessel as described herein).

By "Aβ transport" is meant the transport or clearance of an Aβ peptide from tissue, for example across the BBB, into the circulation. In a synthetic blood vessel system, "Aβ transport" refers or describes the transport of an Aβ peptide from the antelumen into the lumen.

By "Aβ modulator" is meant a compound that inhibits or decreases Aβ deposition or enhances or increases Aβ transport. The increase or decrease may be a change of any value between 10% and 90%, or of any value between 30% and 60%, or may be over 100%, when compared with a control or reference sample or compound. In alternative embodiments, the increase or decrease may over two-fold, or over five-fold, or over 10-fold, or over 100-fold, or over 300-fold, or over 500-fold or over 1000-fold, when compared with a control or reference sample or compound. In some embodiments, the control may be the level of Aβ deposition or Aβ transport in a synthetic blood vessel system, as described herein, in the absence of the test compound. In some embodiments, the control may be monocyte binding.

A "test compound" is any naturally-occurring or artificially-derived chemical or biological compound. Test compounds may include, without limitation, peptides, polypeptides, synthesised organic molecules, naturally occurring organic molecules, antibodies, and nucleic acid molecules. In some embodiments, a test compound can "compete" with or "augment" the activity of a known compound such as a gamma secretase inhibitor, BACE inhibitor, antibodies directed against Aβ, compounds that modulate astrocyte- or pericyte-derived apoE such as but not limited to LXR agonists, compounds that the levels of functional properties of circulating HDL or other circulating blood components by, for example, interfering with Aβ deposition or promoting Aβ transport. Generally, a test compound can exhibit any value between 10% and 200%, or over 500%, modulation when compared to a control or reference compound. For example, a test compound may exhibit at least any positive or negative value from 10% to 200% modulation, or at least any positive or negative value from 30% to 150% modulation, or at least any positive or negative value from 60% to 100% modulation, or any positive or negative value over 100% modulation. In some embodiments, the control may be the level of Aβ deposition or Aβ transport in a synthetic blood vessel system, as described herein, in the absence of the test compound.

By "determining" is meant analysing the effect of a test compound on the synthetic blood vessel. The analysing may include, without limitation, any suitable assay as described herein or known in the art, such as an immunological assay (for example, ELISA or western blotting) or a microscopy assay, such as fluorescence microscopy. In some embodiments, determining the level of monocyte adhesion may include a microscopy assay such as fluorescence microscopy. In some embodiments, determining the level of endothelial cell activation may include measuring the mRNA transcript levels of genes or expression of proteins involved in cell activation (including but not limited to ICAM-1).

By "apolipoprotein E," "apoE" or "ApoE" is meant a lipoprotein that can transport cholesterol and lipids through the bloodstream or the central nervous system. In some embodiments, an apoE protein may have the sequence set forth in NCBI Accession No. AAD02505. In some embodiments, an apoE protein may encompass a full-length protein as well as fragments, isoforms or homologues thereof. Examples of apoE isoforms may include apoE2, apoE3 and apoE4. In some embodiments, an apoE2 isoform may have the sequence set forth in NCBI Accession No. 1NFO_A. In some embodiments, an apoE3 isoform may have the sequence set forth in NCBI Accession No. 1NFN_A. In some embodiments, an apoE4 isoform may have the sequence set forth in NCBI Accession No. 1B68_A. In some embodiments, apoE may contain the L28P mutation (Argyri, L. et al. J Biol Chem. 2014 May 2; 289(18):12931-45). In some embodiments, an apoE protein may be a form of apoE that may result from processing within a cell. In some embodiments, an apoE protein may be a recombinantly expressed apoE, naturally expressed apoE, or an apoE where expression has been induced. In some embodiments, an apoE protein may be a human apoE. In some embodiments, an apoE protein may be obtained from an astrocyte. In some embodiments, an apoE protein may be obtained from a pericyte. In some embodiments, an apoE protein may be obtained from a monocyte or monocyte-derived macrophage. In some embodiments, an apoE protein may be obtained from a microglial cell. In some embodiments, recombinant apoE may be added to the synthetic blood vessel system. In alternative embodiments, apoE expression may be induced within the synthetic blood vessel system by for example, using a compound that stimulates apoE gene expression such as but not limited to a Liver-X-Receptor (LXR) agonist.

By "high-density lipoprotein" or "HDL" is meant a heterogeneous mixture of molecules that may include apoA-I, cholesterol, phospholipids, and various other lipids and proteins found in plasma. HDL molecules can transport cholesterol and other lipids through the bloodstream. In some embodiments, HDL molecules may be isolated from an organism, such as a human or animal. In some embodiments, HDL molecules may be obtained from commercial sources. In some embodiments, HDL molecules may be reconstituted from lipid-free or lipid-poor apolipoproteins.

The synthetic blood vessel may also be used in a method of determining a subject's risk for a cerebrovascular dysfunction by contacting the synthetic blood vessel with an Aβ peptide and a sample from the subject and determining the level of Aβ deposition or transport in the sample, where the subject has an increased risk for a cerebrovascular dysfunction if the level of Aβ deposition is increased or if Aβ transport is reduced. In some embodiments, the method may include predicting the subject's risk of a cerebrovascular dysfunction. In some embodiments, the method may include monitoring the subject's risk of a cerebrovascular dysfunction. In some embodiments, the method may be used to determine the effects of a cardiovascular dysfunction, such as hypertension, by modulating factors such as flow rate and pressure of the circulating medium. In some embodiments, plasma or immune cells from a subject, such as from a specific patient group, can be evaluated for effects on cerebrovascular function, including pre- and post-intervention analyses, to better understand the interactions between cardiovascular factors (e.g. type II diabetes mellitus, hypercholesterolemia, hypertension) and brain factors (e.g., apoE genotype).

A "sample" can be any organ, tissue, cell, or cell extract isolated from a subject, such as a sample isolated from a mammal having a cerebrovascular dysfunction, suspected of having a cerebrovascular dysfunction or at risk for a cerebrovascular dysfunction. For example, a sample can include, without limitation, cells or tissue (e.g., from a biopsy or autopsy) from bone, brain, breast, colon, muscle, nerve, ovary, prostate, retina, skin, skeletal muscle, intestine, testes, heart, liver, lung, kidney, stomach, pancreas, uterus, adrenal gland, tonsil, spleen, soft tissue, peripheral blood, whole blood, red cell concentrates, platelet concentrates, leukocyte concentrates, blood cell proteins, blood plasma, platelet-rich plasma, a plasma concentrate, a precipitate from any fractionation of the plasma, a supernatant from any fractionation of the plasma, blood plasma protein fractions, purified or partially purified blood proteins or other components, serum, semen, mammalian colostrum, milk, urine, stool, saliva, placental extracts, amniotic fluid, lymphatic fluid, a cryoprecipitate, a cryosupernatant, a cell lysate, mammalian cell culture or culture medium, products of fermentation, ascitic fluid, proteins present in blood cells, or any other specimen, or any extract thereof, obtained from a patient (human or animal), test subject, or experimental animal. In some embodiments, it may be desirable to separate cancerous cells from non-cancerous cells in a sample. A sample may also include, without limitation, products produced in cell culture by normal or transformed cells. A sample may also include, without limitation, any organ, tissue, cell, or cell extract isolated from a non-mammalian subject, such as an insect, microbe or a worm. A "sample" may also be a cell or cell line created under experimental conditions, that is not directly isolated from a subject. A sample can also be cell-free, artificially derived or synthesised. The term "plasma" refers to blood collected into tubes containing an anti-coagulant such as but not limited to EDTA or heparin, after which blood cells are removed by centrifugation. Plasma retains all lipoprotein subclasses and coagulation factors. The term "serum" refers to blood collected into tubes containing a clotting resin, allowed to clot, after which blood cells and clotting factors are removed by centrifugation. Serum retains all lipoprotein subclasses. The sample may include HDL or apoE or both. A "control" includes a sample obtained for use in determining base-line expression or activity. Accordingly, a control sample may be obtained by a number of means including from a subject not having a cerebrovascular dysfunction; from a subject not suspected of being at risk for a cerebrovascular dysfunction; or from cells or cell lines derived from such subjects. A control also includes a previously established standard. Accordingly, any test or assay conducted according to the invention may be compared with the established standard and it may not be necessary to obtain a control sample for comparison each time.

By "cerebrovascular dysfunction," as used herein, is meant a dysfunction of the cerebral blood vessels that may lead to changes in tissue structure and/or function and/or in disturbed cerebral blood flow. Cerebrovascular dysfunction may lead to the development of a cerebrovascular disease or disorder including but not limited to type II diabetes mellitus, hypercholesterolemia, hypertension, cerebral amyloid angiopathy (CAA), ischemic brain injury, transient ischemic attack, stroke, dementia, cognitive impairment and Alzheimer's disease (AD). The term "Alzheimer's disease" or AD refers to or describes a neurodegenerative disease typically associated dementia, memory loss, disorientation, mood swings, behavioral issues, accumulation of Aβ plaque deposits and neurofibrillary tangles within the brain.

The synthetic blood vessel may also be used to determine whether a compound or drug is suitable for delivery to the brain by, for example, contacting the lumen of a synthetic blood vessel, such as a tripartite or more complex synthetic blood vessel (e.g., quadripartite or pentapartite) with a test compound and determining the level of transport of the test compound to the antelumen of the synthetic blood vessel, where the test compound is suitable for delivery to the brain if it is transported to the antelumen of the tripartite vessel. In some embodiments, a synthetic blood vessel, such as a tripartite or more complex synthetic blood vessel (e.g., quadripartite or pentapartite) may be used to evaluate the penetration of a compound through the BBB by, for example, contacting the lumen of the synthetic blood vessel with a test compound and determining the presence or absence, or quantifying the amount, of the test compound in the antelumen, using any suitable technique as described herein or known in the art, such as for example, mass spectroscopy.

The synthetic blood vessel may be provided in a kit together with an amyloid beta (Aβ) peptide and instructions for use. The kit may further include a lipoprotein or a monocytic cell or both.

Figure 10:
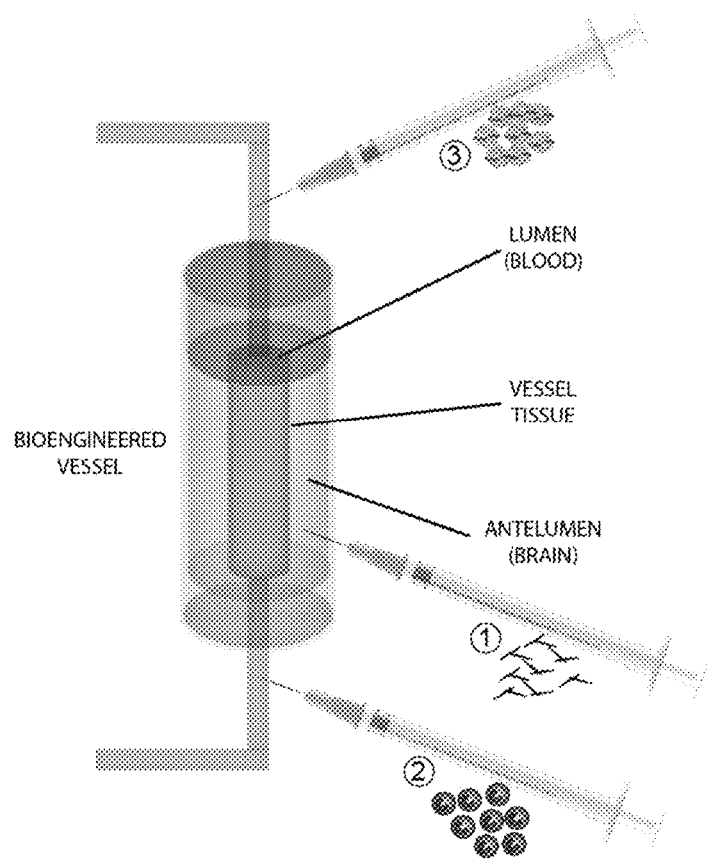
FIG. 10 is a schematic of an exemplary synthetic blood vessel system, where 1) corresponds to a "brain" compound, such as Aβ or apoE, 2) refers to a cell that may be applied to the synthetic blood vessel (such as a monocyte) and 3) refers to a circulating compound, such as HDL.

A schematic diagram of an exemplary synthetic blood vessel is shown in FIG. 10. As shown in FIG. 10, a synthetic blood vessel (bioengineered vessel) with a lumen, which corresponds to the circulatory system or blood, and an antelumen, which corresponds to the brain, is coupled to a flow system. In this example, Aβ peptide (1) can be added to the antelumen (brain) and injectable cells, such as monocytes (2) and/or circulating compounds, such as HDL (3) can be added to the flow system/lumen and assays, as described herein or known in the art, may be performed.

The present invention will be further illustrated in the following examples.

EXAMPLES

Materials and Methods

In Vitro Fabrication of Tissue Engineered Vascular Grafts

Bioengineered constructs were fabricated using a dynamic, semi-pulsatile flow bioreactor system. Tubular biodegradable scaffolds with lengths of 1.5 cm and inner diameters of 2 mm were produced. Briefly, non-woven polyglycolic acid (PGA, Biomedical Structure) meshes (thickness: 1 mm and density: 70 mg/cc) were dip-coated with polycaprolactone (PCL) and polylactate (PLA) by dipping PGA mesh in a solution of 1.75% (w/w) PCL/PLA/tetrahydrofuran (THF) solution (Sigma Aldrich), shaped into tubes using heat, and externally coated with a 10% PCL/THF (w/w) solution. Scaffolds were sterilized by immersion in 70% ethanol for 30 min followed by three phosphate buffered saline (PBS) washes and then immersion in advanced Dulbecco's modified eagle medium (DMEM) supplemented with 10% fetal bovine serum (FBS) for at least 12 h. Human umbilical cord myofibroblasts (UCMFB) were seeded at density of $2-3\times10^6$ cells/cm$^2$ on the inner surface of the scaffold using fibrin (fibrinogen 10 mg clottable protein/ml PBS and thrombin 100-10 mU/ml PBS) as a cell carrier that was added directly to the scaffold, then incubated under static conditions for a minimum of 3 days before exposure to dynamic flow. The flow of nutrient medium (Advanced DMEM supplemented with 10% FBS, 1% L-glutamine and 0.05% Pen/Strep) was directed through the lumen of the bioreactor circulation loop to mimic blood flow for a minimum of one week. Vascular intermediates were then seeded with umbilical vein endothelial cells (HUVEC) ($1\times10^6$ cells/cm$^2$) and cultivated first in static conditions for a minimum of 5 days in EGM™-2 supplemented as above. For bipartite vessels, after the static phase, vascular grafts were placed back in the bioreactor for minimum of 10 additional days with increasing medium flow to a final rate of 10 ml/min by the 10th day). For tripartite vessels, after the static phase after HUVEC addition, primary astrocytes were seeded ($1\times10^6$ cells/cm2) using fibrin as a cell carrier as above on the antelumen side of the tissue. After 5 min at RT, grafts were placed under flow conditions with EGM-2 supplemented as above in the circulation chamber and complete astrocyte medium in the tissue chamber for a minimum of 10 additional days with increasing medium flow to 10 ml/min by the lath day. For quadripartite culture, after seeding the astrocytes, grafts were kept for 24 h in 10% FBS complete EGM2 media under static condition. 2-$4\times10^6$ cells/cm) IPSC derived neurons (days 50-110) were seeded on the anteluminal side of the tissue using matrigel as cell carrier. Grafts were held for 5 minutes with forceps before placing them under flow conditions with neuron media (N2 media: 48 ml DMEM/F12, 1% N2 supplement, 5 µg/ml insulin, 1% L-glutamine, 1% modified eagle medium (MEM)-nonessential amino acids (NEAA), 0.18% 55 mM2-ME and 1% penicillin/streptomycin (P/S)) in the circulation and tissue chamber for 10-30 additional days with increasing medium flow to 10 ml/min by the 10th day.

Preparation of Beta Amyloid Peptides

Recombinant Aβ40 and Aβ42 peptides (California Peptide) were dissolved in hexafluoroisopropanol (HFIP). The HFIP was removed by evaporation overnight and stocks were stored at −20° C. On the day of the assay, soluble monomers were prepared by reconstituting the peptide film in dimethylsulfoxide (DMSO) to 5 mM, diluted further to 100 µM in Roswell Park Memorial Institute (RPMI) medium without FBS. 100 µl of Aβ solution was injected in the tissue chamber containing 900 µl of DMEM (Gibco) without FBS to the desired concentration using a syringe under flow conditions. For luminal recovery, 100 µl circulating medium was collected at the indicated time.

Lipoproteins

All experiments were conducted under an approved clinical protocol (UBC Clinical Ethics Research Board H14-03357). Upon receipt of written informed consent, 100 ml of fasted blood was collected from normolipidemic healthy donors into vacutainer tubes containing EDTA. Plasma HDL (1.063-1.21 g/ml) was isolated by sequential potassium bromide gradient ultracentrifugation. The purity of the HDL preparations were verified by sodium dodecyl sulfate polyacrylamide gel electrophoresis (SDS-PAGE) followed by Coomassie blue staining to ensure no low-density lipoprotein (LDL) or albumin contamination. Total protein concentration was assessed using the bicinchoninic acid (BCA) assay (Thermofisher Scientific). Recombinant ApoE2 and ApoE4 were commercially purchased and solubilized following the manufacturer's instructions (ABCAM, apoE2 ab55210 and apoE4 ab50243). Secretion of endogenous ApoE from human astrocytes in tripartite vessels was induced by injecting 0.8 µM GW3965 in the circulation medium 72 h prior to addition of Aβ. ApoE concentrations were measured using enzyme linked immunosorbent assay (ELISA) as previously described (Fan et al. 2016 PLoS One. September 6; 11(9):e0162384). Briefly, ELISA plates were coated overnight with anti-human ApoE mAB E276 antibody (MabTech) at 1.55 µg/mL in PBS at 4° C., washed two times with PBST (0.05% Tween 20 in PBS), and blocked with 0.1% Blocker A (Meso Scale Discovery) in PBST. After 1 h incubation at RT and two washes with PBST, medium or human recombinant ApoE standard (MabTech) were added to each well. After 1 h at RT and two subsequent PBST washes, biotinylated anti-human ApoE monoclonal antibody E887 (MabTech) was added to each well at a concentration of 0.5 µg/mL in blocking buffer. After 1 h at RT, plates were washed before adding QuantaBlue Substrate (Pierce) working solution (9 parts of Substrate Solution to 1 part Stable Peroxide Solution). Fluorescence was read after 15 min at RT on an EnSpire 2300 Multilabel Plate Reader ($325_{Ex}/420_{Em}$).

NO Measurement

Nitric oxide (NO) synthesis was measured using a commercial nitric oxide synthesis (NOS) activity assay kit (Caymenchemical). Briefly, a 2-3 mm ring of vascular tissue was mechanically ground in 150 µl of ice-cold homogenized buffer (25 mM Tris-Cl, pH7.4, 1 mM EDTA and 1 mM EGTA) and centrifuged 15 min at 4° C. at 10,000 g. The supernatant was aliquoted and incubated in reaction buffer containing 25 mM Tris-Cl, pH7.4, 0.25 mM EDTA, 0.6 mM CaCl$_2$, 1 mM NADP, 200 nM calmodulin, 3 µM tetrahydrobiopterin, 1 µM flavin adenine dinucleotide, 1 µM flavin adenine monoucleotide and 0.2 µCi L-$^3$H-arginine; PerkinElmer) in the presence of 10 nM acetylcholine (Ach), 0.2 mg/ml HDL or 1 mM L-NG-nitroarginine methyl ester (L-NAME). After 60 min at 37° C., the reaction was stopped by adding 400 µl of stop buffer (50 nM HEPES, 5 mM EDTA, pH 5.5). The solution was loaded onto an ion exchange column equilibrated with stop buffer to separate L-$^3$H-citruline from L-$^3$H-arginine. Scintillation mix (Ultimate Gold, PerkinElmer) was added to the supernatant and counted using LS6500 β-counter (Beckman Coulter). The percent citrulline formed was calculated as follows: % conversion=(cpm reaction-cpm background)/cpm total*100.

Aβ Quantification

Luminal medium was collected from the circulation chamber and 5 mm tissue rings were crushed and lysed in radioimmunoprecipitation assay (RIPA) buffer (10 mM Tris pH 7.4, 150 mM NaCl, 1.0% NP-40, 1.0% sodium deoxycholate, 0.1% SDS and cOmplete protease inhibitor with EDTA (Roche)). Aβ40 (KHB3442, Life Tech) and Aβ42 (KHB3482, Life Tech) were quantified using commercial ELISAs and normalized to total protein concentration, measured by BCA.

Preparation of Plasma, HDL and PBMCs

All experiments were conducted under an approved clinical protocol (UBC Clinical Ethics Research Board H14-03357). Upon receipt of written informed consent, 100 ml of fasted blood was collected from normolipidemic healthy donors into vacutainer tubes containing K2-EDTA as an anticoagulant and centrifuged to remove blood cells. Plasma HDL (1.063-1.21 g/ml) was isolated by sequential potassium bromide gradient ultracentrifugation as described (Robert et al. 2013 Arterioscler Thromb Vasc 33(12):2699-70624115033). The purity of the HDL preparations was verified by sodium dodecyl sulphate-polyacrylamide gel electrophoresis (SDS-PAGE) followed by Coomassie blue staining to ensure no low-density lipoprotein (LDL) or albumin contamination. Eight independent donors were used across the experiments, 6 isolated in-house and 2 commercially obtained (Leebioscience). Human-derived, lipid free apoA-I was a kind gift from CSL-Behring. Primary human PBMC were isolated from healthy donors by centrifugation on a continuous density gradient (Lymphoprep™, Stemcell) following the manufacturer's instructions. Freshly isolated PBMC were fluorescently labeled with 10 μM of Cell-Tracker Red for 30 min (Invitrogen) following the manufacturer's recommendations.

Monocyte Adhesion in Engineered Vessels

Vascular grafts were perfused with complete EGM-2 with 2% FBS. 1 μM Aβ42 or Aβ40 monomers were injected directly into the graft chamber to mimic Aβ originating from the brain (antelumen) side of the vessel. At time points ranging from 2-72 h, immortalized human monocytes (THP1, ATCC) were fluorescently labeled with Cell-Tracker Red as described above, injected in the graft circulation at a concentration of $1\times10^6$ cells/ml and maintained under flow conditions for 3 hours. For HDL experiments, vascular grafts were perfused with luminal HDL (200 μg/ml) for 2 h before injecting Aβ in the antelumen side for 8 h. Tissues were longitudinally cut open, washed extensively with PBS and fixed with 4% PFA. After 20 min, tissues were washed 3 times with PBS and mounted in Prolong Gold antifade reagent with DAPI. Adherent monocytes were quantified using a SP8 confocal microscope (Leica).

Testing of Plasma Samples in Vessel System

Bipartite vessels were prepared as described above. After 4 weeks in culture, Aβ42 was injected within the tissue chamber (antelumen) in the absence or presence of either luminal HDL (200 μg/ml), plasma from a healthy donor (25% volume plasma and 75% volume of endothelial medium) or plasma from a type-2 diabetic patient (labelled as T2DM patient) (25% volume plasma and 75% volume of endothelial medium).

Immunostaining of Quadripartite Vessels

After 21 days in culture, quadripartite vessels were fixed using 4% paraformaldehyde (PFA) for 20 minutes, washed three times with PBS, stained and imaged using inverted confocal microscopy to visualize the surface of intact tissue, or after cryopreservation in 40% sucrose in PBS solution and freezing in 5% bovine gelatin before sectioning at 20 μm to examine cross-sections of the tissue. Sections were immunostained against cluster of differentiation 31 (CD31; EC marker) α-smooth muscle actin (α-SMA actin; SMC marker), glial fibrillary acidic protein (GFAP; astrocyte marker) or microtubule associated protein 2 (MAP2) and β-tubulin III (neuron markers) and synapsin (synapse marker).

Testing of Neuronal Functionality

After 21 days in culture, quadripartite tissue were harvested in Hanks buffered salt solution (HBSS) and cut in half. One half is incubated in HBSS without potassium chloride (KCl) and one half in HBSS with 50 nM KCl. After 30 minutes buffer was collected and run through a GABA/glutamate affinity column on a high pressure liquid chromatography (HPLC) previously calibrated with glutamate standard (0 to 2.5 uM).

Example 1—Structural and Functional Characterisation of Tripartite Bioengineered Cerebral Vessels Bipartite vessels consisting of ECs and SMCs resemble peripheral or leptomeningeal, rather than cortical, vessels. Accordingly, to extend the translational relevance of bioengineered vessels, we incorporated human primary astrocytes on the antelumen. As the diameter of the vessels is approximately 2 mm prior to cell seeding, and further contains muscular cells, our bioengineered tripartite vessels were designed to resemble larger human penetrating arteries rather than the microvasculature. Morphology of the vessel was confirmed by immunostaining against CD31 to confirm the presence of an EC monolayer on the luminal side of tripartite vessels. The expression of α-smooth muscle actin (α-SMA actin) confirmed the smooth muscle phenotype of cells in the inner layers, and the expression of GFAP confirmed the presence of astrocytes on the antelumenal layers of bioengineered tripartite vessels. Higher magnification images revealed GFAP-positive protrusions penetrating into the tissue suggestive of astrocyte end-feet like structures, which were also positive for aquaporin 4.

The EC barrier was further analysed using immunostaining against the tight junction proteins ZO1, ZO2 and claudin 5, as well as the BBB-specific glucose transporter 1 (glut-1). The results indicated that peripherally-derived ECs (HUVEC) become brain-like, when cultured in the presence of astrocytes and under flow conditions.

The integrity of the endothelial barrier in tripartite vessels was functionally assessed by injecting Evans blue into the circulation loop and compared to bipartite vessels. As expected, Evans blue was excluded in both tripartite and bipartite vessels (FIG. 1A).

The functionality of EC and astrocytes within tripartite bioengineered vessels was evaluated by measuring nitric oxide (NO) produced by EC and native apoE secreted by astrocytes, which were genotyped as apoE3/apoE3. To determine NO production, vessels were incubated with either 10 nM of acetylcholine (Ace) or 200 μg/ml of HDL for 60 minutes before measuring conversion of L-$^3$H-arginine to L-$^3$H-citruline. A significant increase was measured after both treatments, whereas in the presence of the specific NO synthase inhibitor L-NG-nitroarginine methyl ester (L-NAME), the conversion was blocked (FIG. 1A)

For apoE secretion, brain-penetrant Liver-X-Receptor (LXR) GW3965 was circulated through the lumen of the vessels 72 h before collecting medium. ELISA quantification demonstrated that GW3965 (GW) significantly stimulated the secretion of native apoE in the tripartite vessels (FIG. 1I). These data confirmed that our tripartite bioengineered tissue has both structural and functional characteristics of native cerebral arteries.

Figure 2A:
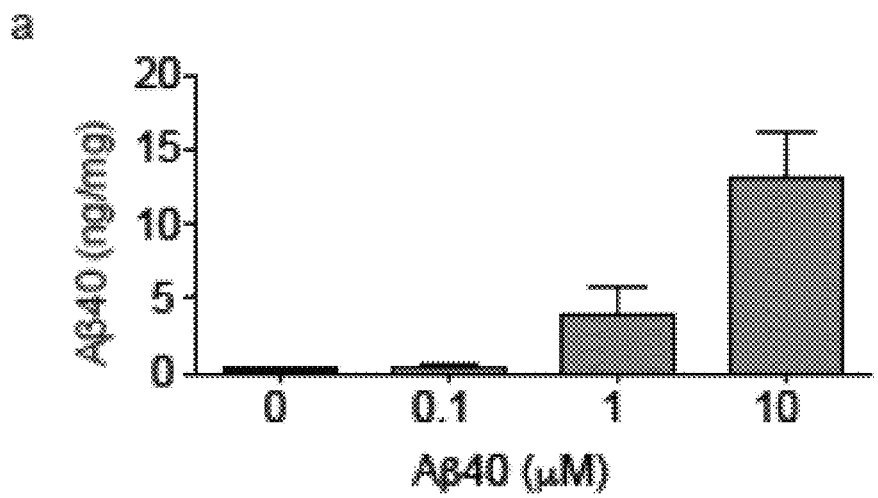
FIG. 2A is a bar graph showing Aβ40 accumulation within and transport through bipartite vessels using ELISA.
Figure 2B:
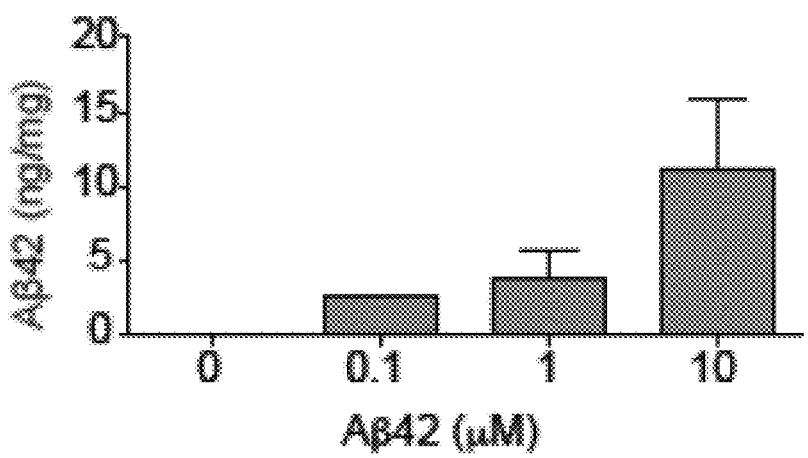
FIG. 2B is a bar graph showing Aβ42 accumulation within and transport through bipartite vessels using ELISA.
Figure 2C:
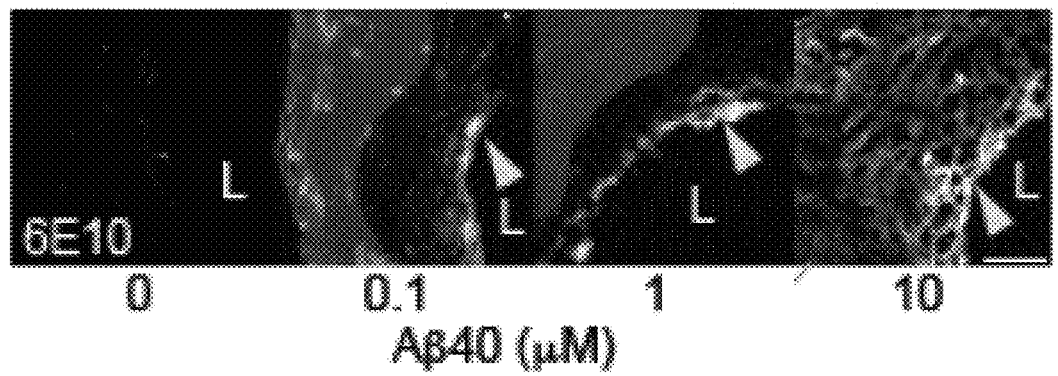
FIG. 2C is a micrograph showing Aβ40 accumulation within and transport through bipartite vessels using immunostaining with the anti-Aβ antibody 6E10.
Figure 2D:
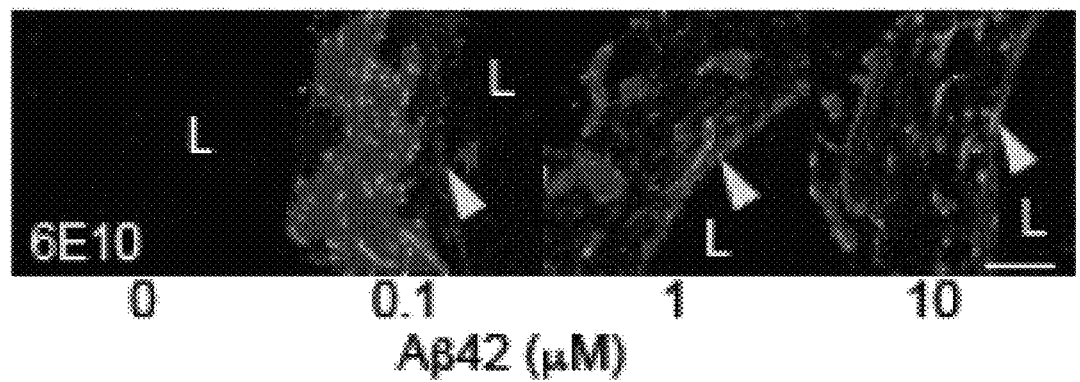
FIG. 2D is a micrograph showing Aβ42 accumulation within and transport through bipartite vessels using immunostaining with the anti-Aβ antibody 6E10.
Figure 2E:
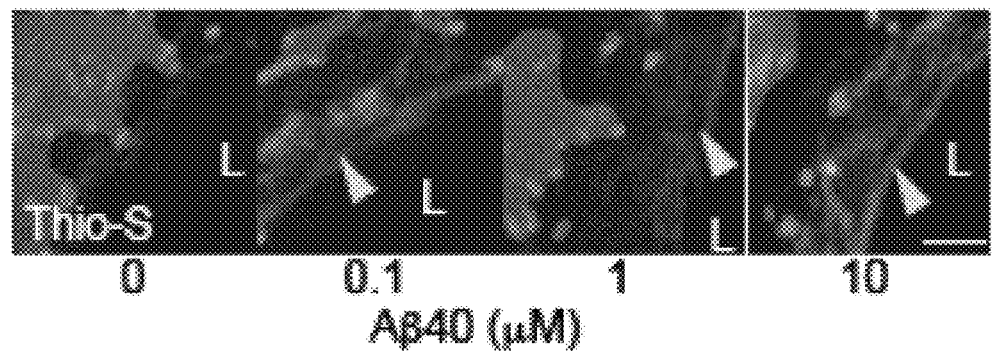
FIG. 2E is a micrograph showing Aβ40 accumulation within and transport through bipartite vessels using Thioflavin-S staining.
Figure 2F:
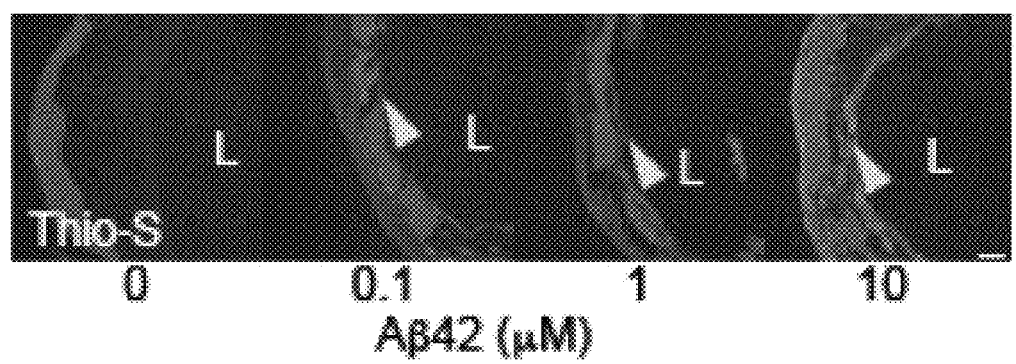
FIG. 2F is a micrograph showing Aβ42 accumulation within and transport through bipartite vessels using Thioflavin-S staining.
Figure 2G:
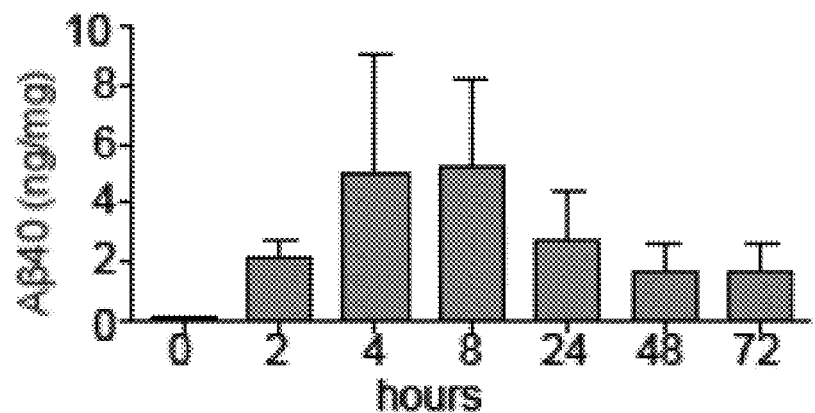
FIG. 2G is a bar graph showing the kinetics of CAA formation based on Aβ40 accumulation using ELISA.
Figure 2H:
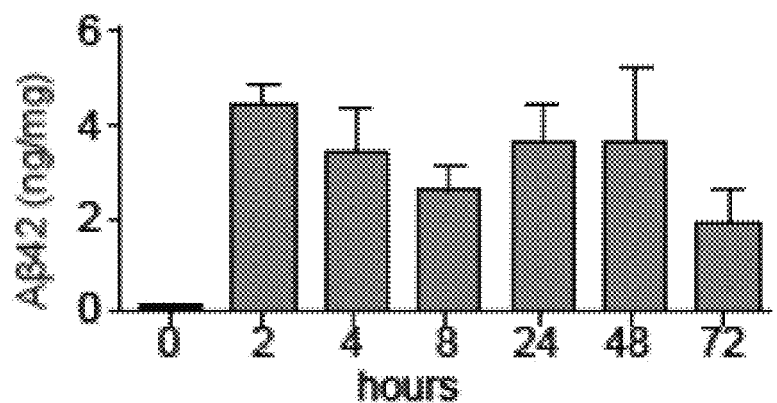
FIG. 2H is a bar graph showing the kinetics of CAA formation based on Aβ42 accumulation using ELISA.
Figure 2I:
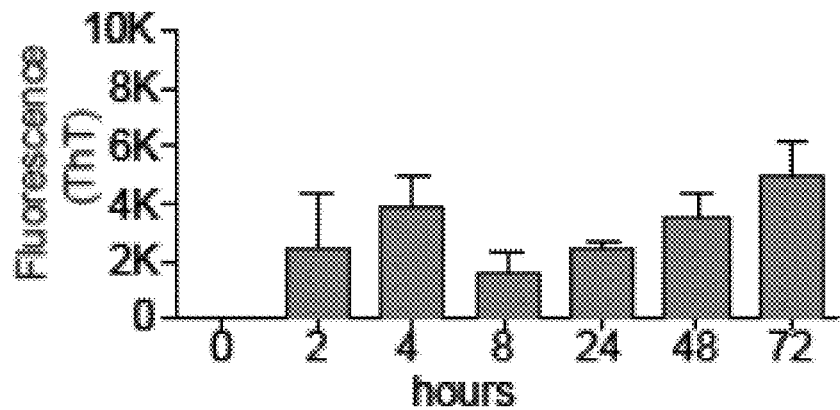
FIG. 2I is a bar graph showing the kinetics of CAA formation based on Aβ40 accumulation using Thioflavin-T staining.
Figure 2J:
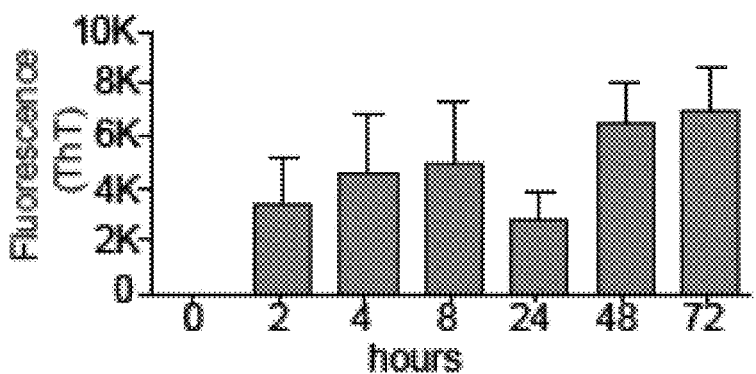
FIG. 2J is a bar graph showing the kinetics of CAA formation based on Aβ42 accumulation using Thioflavin-T staining.
Figure 2K:
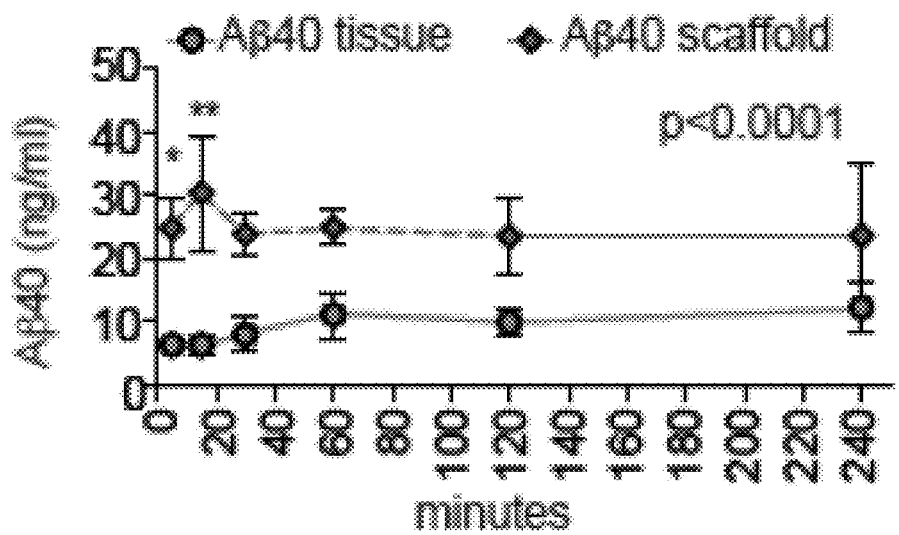
FIG. 2K is a line graph showing Aβ40 transport using ELISA.
Figure 2L:
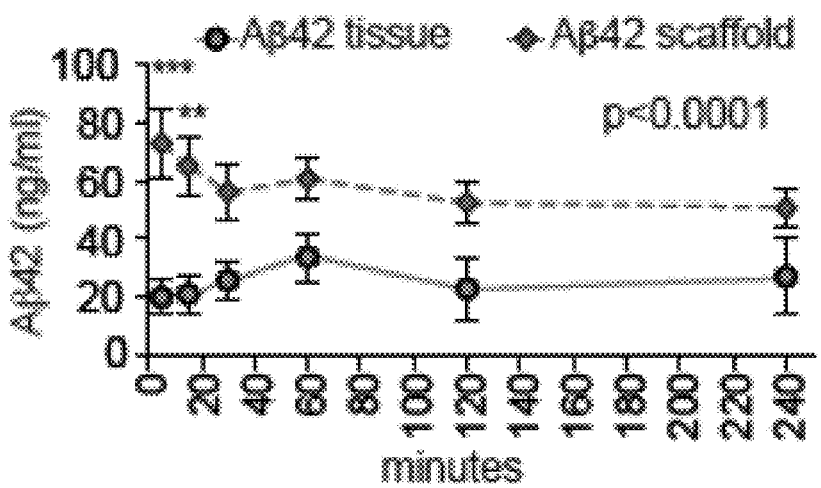
FIG. 2L is a line graph showing Aβ42 transport using ELISA.

Example 2—Monomeric Aβ Accumulates and Aggregates in Bioengineered Bipartite Vessels and Aβ is Transported Across Bioengineered Vessels Accumulation of Aβ within cerebral vessel walls, known as cerebral amyloid angiopathy (CAA), is a common pathological feature in AD. To determine if the bioengineered vessels model CAA, we injected monomeric Aβ40 or Aβ42 on the anteluminal side of the vessel to mimic native conditions where Aβ is predominantly produced by neurons. More specifically, Aβ40 and Aβ42 monomers (0, 0.1, 1.0 and 10 μM) were injected into the tissue chamber (antelumen) and incubated for 48 h under flow conditions (FIGS. 2A-F). Aβ deposition within bioengineered vessels was measured using ELISA (FIGS. 2A-B), immunostaining with the anti-Aβ antibody 6E10 Aβ (FIGS. 2C-D), and Thioflavin-S staining (FIGS. 2E-F). To determine the kinetics of CAA formation, Aβ40 and Aβ42 monomers (1 μM) were injected into the tissue chamber and incubated for the indicated times before measuring Aβ tissue concentrations by ELISA (FIGS. 2G-H) or aggregation within the tissue using Thioflavin-T (FIGS. 2I-J). Aβ transport was measured after injecting Aβ40 and Aβ42 monomers (1 μM) into the anteluminal chamber and sampling media from the circulation (lumenal) chamber at the indicated times (FIGS. 2K-L).

Both ELISA (FIGS. 2A-B) and 6E10 immunostaining (FIGS. 2C-D) confirmed dose-dependent retention of Aβ40 and Aβ42 within the bioengineered vessel wall 48 h after injection (arrowhead), which could be distinguished from autofluorescence of the residual scaffold material. As Aβ fibrillization within the vessel wall is an important feature of CAA, we also stained vessels using Thioflavin-S, and confirmed dose-dependent fibrillization in the bioengineered vessels (FIGS. 2E-F). We further characterized the time course of Aβ accumulation in bioengineered vessels after anteluminal injection of 1 μM of monomeric Aβ40 or Aβ42. Both ELISA quantification and 6E10 immunostaining revealed Aβ deposition by 2 h after injection, after which Aβ levels remained stable up to 72 h thereafter (FIGS. 2G-H). Interestingly, quantification of beta-sheet formation in bioengineered tissue lysates with Thioflavin-T revealed increasing signal over time, biochemically confirming beta-sheet structures after Aβ seeding (FIGS. 2I-J), confirming increased Aβ fibrillization within bioengineered vessels. These data provide strong support that bioengineered human vessels can be used as an in vitro model of CAA.

A major route of Aβ egress from the brain is direct transport across the cerebral vessel into the circulation. We therefore evaluated the suitability of the bioengineered vessels to analyze "brain-to-blood" Aβ transport by injecting Aβ into the anteluminal tissue chamber compartment of bipartite vessels (or scaffold-only controls), and measured recovered Aβ in the circulating medium over 4 h. ELISA quantification revealed that both Aβ40 and Aβ42 were transported at a slower rate in bioengineered vessels, whereas Aβ freely diffused across scaffold-only controls (FIGS. 2K-L). Taken together, these data demonstrated the feasibility of bioengineered human vessels to study Aβ recovery in the circulation.

Figure 3A:
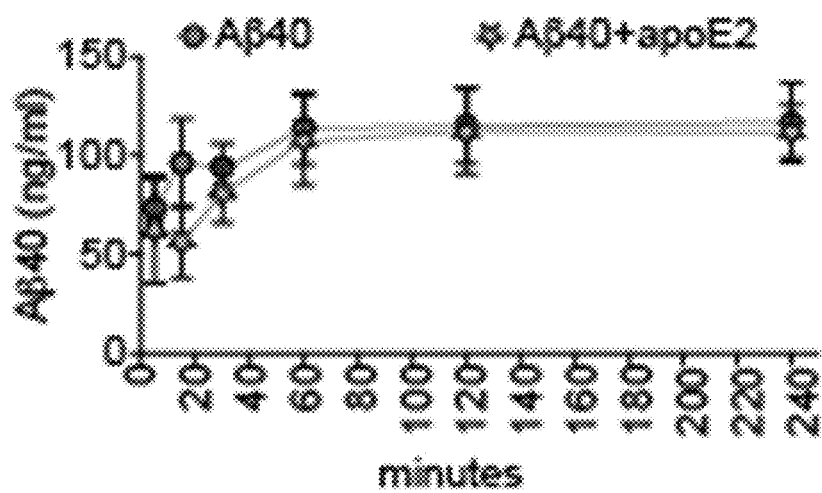
FIG. 3A is a line graph showing the effect of recombinant (r)apoE on Aβ40 transport into luminal circulating medium using ELISA.
Figure 3B:
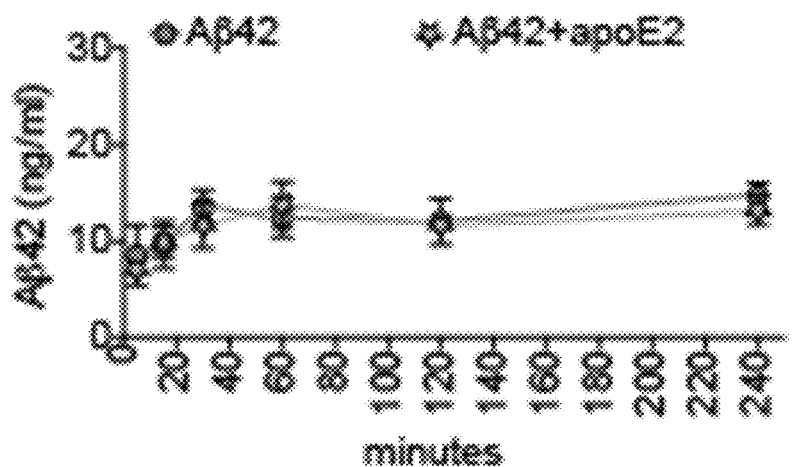
FIG. 3B is a line graph showing the effect of rapoE2 on Aβ42 transport into luminal circulating medium using ELISA.
Figure 3C:
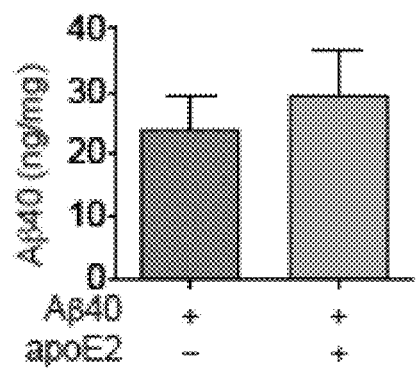
FIG. 3C is a bar graph showing the effect of rapoE2 on Aβ40 accumulation in vascular tissue using ELISA.
Figure 3D:
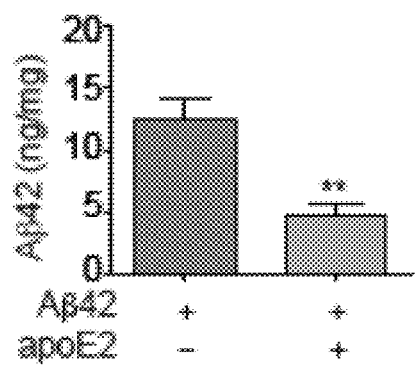
FIG. 3D is a bar graph showing the effect of rapoE2 on Aβ42 accumulation in vascular tissue using ELISA.
Figure 3E:
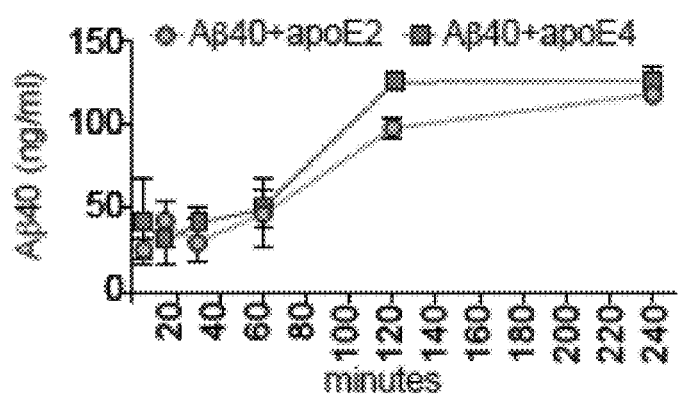
FIG. 3E is a line graph showing the effect of rapoE2 or rapoE4 on Aβ40 transport into luminal circulating medium using ELISA.
Figure 3F:
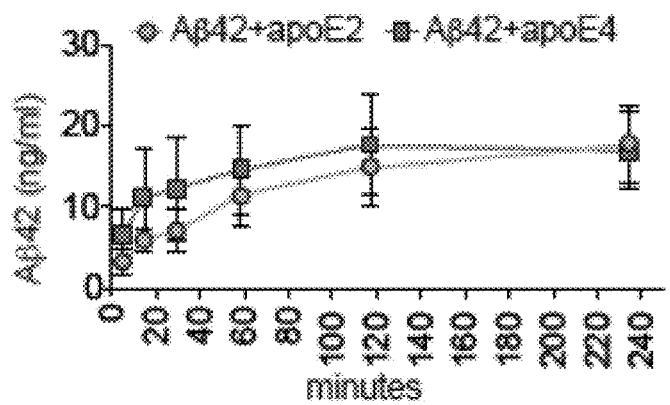
FIG. 3F is a line graph showing the effect of rapoE2 or rapoE4 on Aβ42 transport into luminal circulating medium using ELISA.

Example 3—ApoE Isoform Differentially Reduces Amyloid Accumulation in Bipartite Tissue Genetic variation in APOE represents a common genetic risk for AD, with apoE4 considered detrimental and apoE2 protective (Zlokovic, 2013 JAMA Neurol 70(4):440-444). To test whether apoE regulates vascular Aβ accumulation or transport into the circulation, we injected Aβ40 or Aβ42 in the absence or presence of recombinant apoE2 into the tissue chamber at a molar ratio 25:1 to mimic the relative concentrations in brain CSF. More specifically, Aβ40 and Aβ42 monomers (1 μM) were incubated without or with recombinant apoE (ratio 25:1) for 2 h at 37° C. before injection into the antelumenal tissue chamber. The levels of transported Aβ was measured by ELISA from samples collected from the lumenal circulating medium at the indicated times over 4 h (FIGS. 3A-B), and from vascular tissue collected 24 h after Aβ injection (FIGS. 3C-D). Aβ40 and Aβ42 monomers (1 μM) were incubated without or with recombinant apoE2 or apoE4 (ratio 25:1) for 2 h at 37° C. before injection into the tissue chamber and evaluating transported (FIGS. 3E-F) and accumulated (FIGS. 3G-H) Aβ levels as above. Graphs represent mean±SEM for at least four independent experiments. * p=0.05,  p=0.01 and * p=0.001.

Figure 3G:
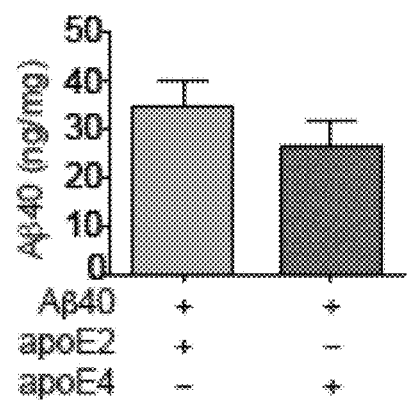
FIG. 3G is a bar graph showing the effect of rapoE2 or rapoE4 on Aβ40 accumulation in vascular tissue using ELISA.
Figure 3H:
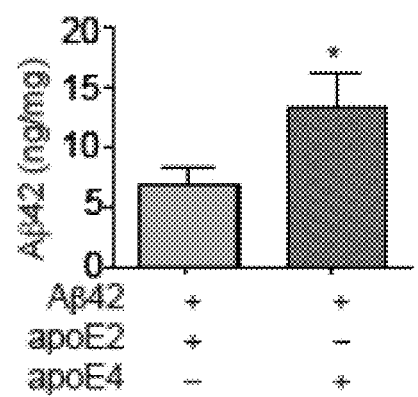
FIG. 3H is a bar graph showing the effect of rapoE2 or rapoE4 on Aβ42 accumulation in vascular tissue using ELISA.

Although apoE2 did not alter the rate of recovery of Aβ into the circulation medium over 4 h (FIGS. 3A-B), apoE2 selectively decreased the amount of Aβ42 deposited into the bioengineered tissue by 24 h (FIGS. 3C-D). We then analyzed whether apoE genotype differentially regulates Aβ transport or tissue accumulation by injecting either recombinant apoE2 or apoE4 with Aβ. Although apoE isoform did not significantly affect the rate of recovery of either Aβ40 or Aβ42 into the circulation medium (FIGS. 3E-F), the tissue accumulation of Aβ42 was again selectively elevated when co-injected with apoE4 at 24 h (FIGS. 3G-H).

Example 4—Circulating HDL Reduces Aβ Accumulation in Bipartite Bioengineered Vessels, and Facilitates Aβ Transport in the Presence of Anteluminal apoE To determine whether circulating HDL can promote Aβ recovery into the circulation and reduce its accumulation in bioengineered vessels, 200 μg/ml of HDL isolated from normolipidemic young donors were perfused through bioengineered vessels immediately after injecting Aβ in the antelumenal space. More specifically, Aβ40 and Aβ42 monomers (1 μM) were injected into the anteluminal chamber in the absence or presence of 200 μg/ml of circulating HDL. The levels of transported Aβ was measured by ELISA from samples collected from the lumenal circulating medium at the indicated times over 4 h (FIGS. 4A-B), and from vascular tissue collected 24 h after Aβ injection (FIGS. 4C-D). Aβ40 and Aβ42 monomers (1 μM) were incubated without or with recombinant apoE (ratio 25:1) for 2 h at 37° C. before injecting into the tissue chamber in the absence or presence of 200 μg/ml of circulating HDL and evaluating transported (FIGS. 4E-F) and accumulated (FIGS. G-H) Aβ levels, as above. Graphs represent mean±SEM for at least four independent experiments. *, § and # p=0.05, ## and  p=0.01 and * p=0.001.

Figure 4A:
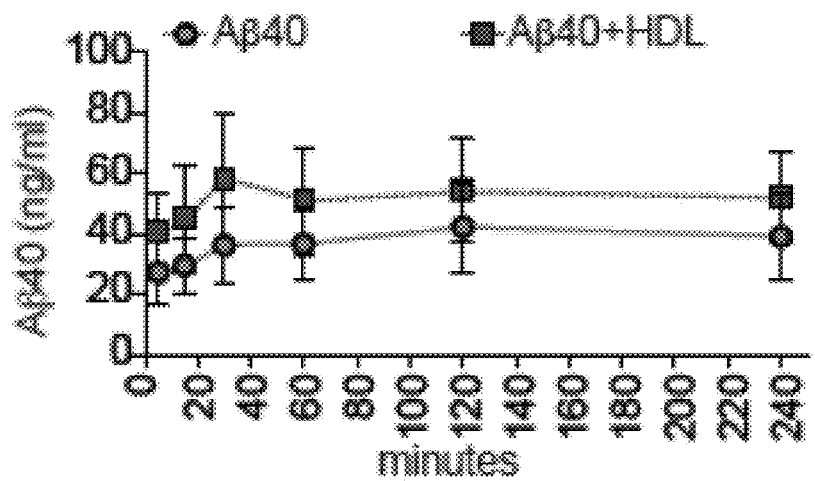
FIG. 4A is a line graph showing the effect of circulating HDL on Aβ40 transport in luminal circulating medium in bipartite vessels using ELISA.
Figure 4B:
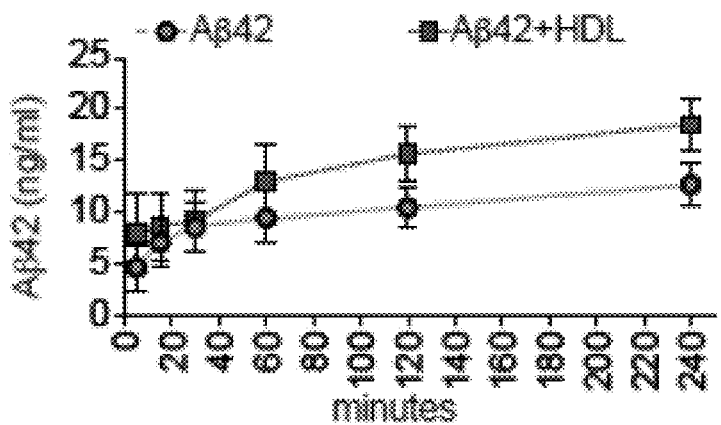
FIG. 4B is a line graph showing the effect of circulating HDL on Aβ42 transport in luminal circulating medium in bipartite vessels using ELISA.
Figure 4C:
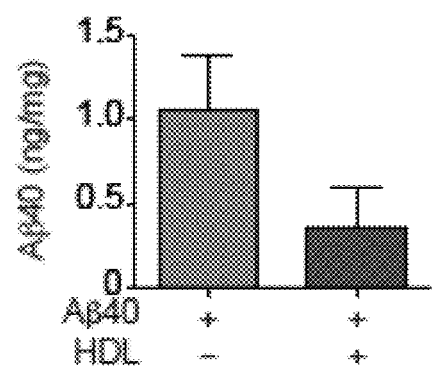
FIG. 4C is a bar graph showing the effect of circulating HDL on Aβ40 accumulation in vascular tissue in bipartite vessels using ELISA.
Figure 4D:
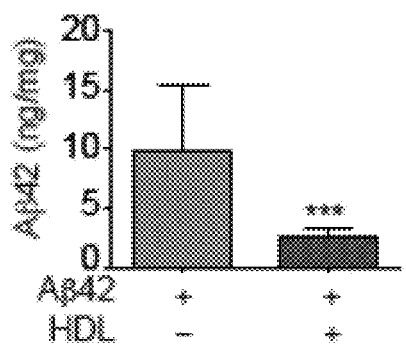
FIG. 4D is a bar graph showing the effect of circulating HDL on Aβ42 accumulation in vascular tissue in bipartite vessels using ELISA.
Figure 4E:
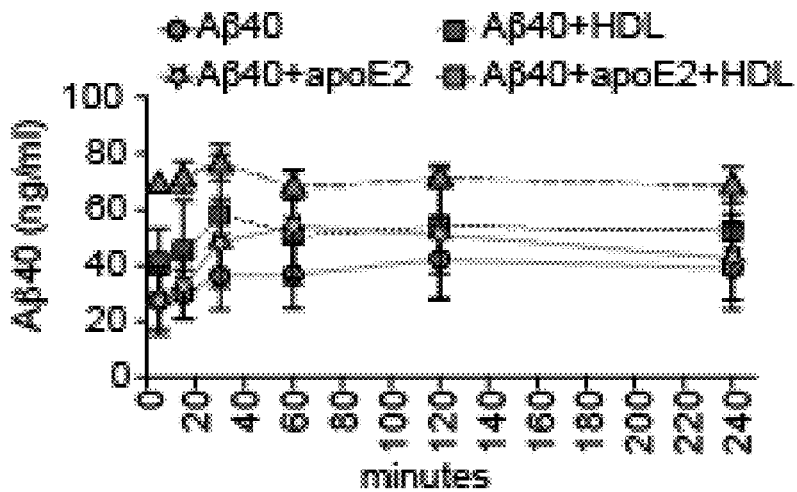
FIG. 4E is a line graph showing the effect of circulating HDL and rapoE2 on Aβ40 transport into luminal circulating medium in bipartite vessels using ELISA.
Figure 4F:
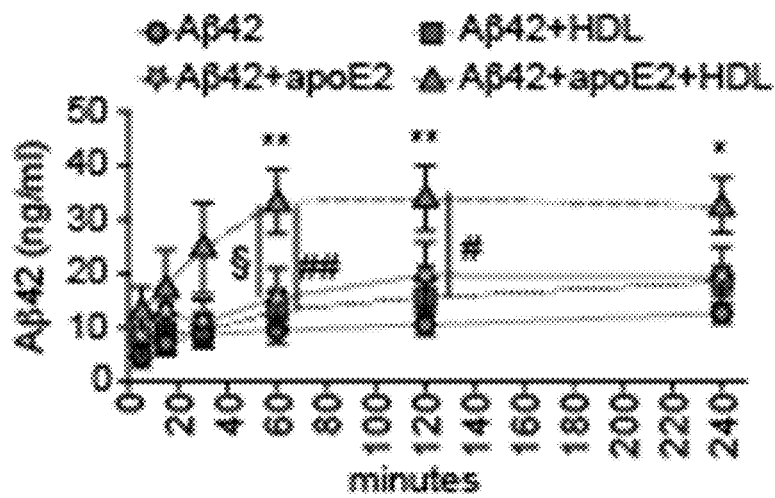
FIG. 4F is a line graph showing the effect of circulating HDL and rapoE2 on Aβ42 transport into luminal circulating medium in bipartite vessels using ELISA.
Figure 4G:
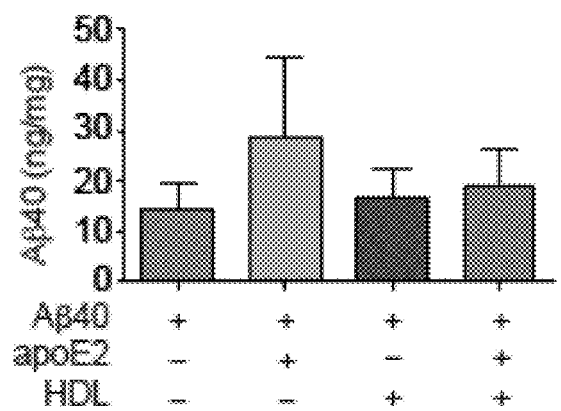
FIG. 4G is a bar graph showing the effect of circulating HDL and rapoE2 on Aβ40 accumulation in vascular tissue in bipartite vessels using ELISA.
Figure 4H:
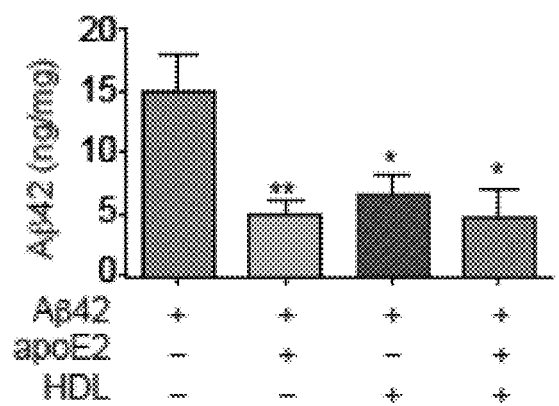
FIG. 4H is a bar graph showing the effect of circulating HDL and rapoE2 on Aβ42 accumulation in vascular tissue in bipartite vessels using ELISA.

Over 4 h, the levels of Aβ42 and Aβ42 recovered in the circulation medium were slightly increased in the presence of HDL but did not reach significance (FIGS. 4A-B). By 24 h, we observed a strong trend toward decreased tissue levels of accumulated Aβ40 and significantly lower accumulated Aβ42 in the presence of HDL (FIGS. 4C-D). We then tested for a functional interaction between apoE and HDL by analyzing Aβ transport and tissue accumulation after injecting recombinant apoE2 into the anteluminal tissue chamber and injecting HDL into the circulating medium. Importantly, the combination of antelumenal apoE2 and circulating luminal HDL showed a strong trend toward increased Aβ40 transport and significantly increased Aβ42 transport over 4 h compared to either Aβ alone or Aβ with apoE or HDL alone over 4 h after injection (FIGS. 4E-F). Consistent with our previous observations at 24 h, the levels of Aβ40 accumulated in the tissue were not significantly affected by apoE2, HDL, or both apoE and HDL (FIG. 4G), but the levels of accumulated Aβ42 were significantly reduced by apoE2, HDL, and in the presence of both apoE and HDL (FIG. 4H). These results strongly support a cooperative role between brain apoE and circulating HDL to preferentially clear Aβ across the vasculature.

Example 5—Circulating HDL in Combination with Astrocyte apoE Promotes Aβ42 Transport Across Tripartite Bioengineered Cerebral Vessels As the combination of recombinant apoE injected into the antelumen tissue chamber and HDL injected into the circulating medium significantly increased Aβ40 and Aβ42 transport and reduced Aβ42 tissue accumulation in bipartite vessels (FIGS. 3A-H and 4A-H), we tested for functional synergy of these lipoproteins in tripartite cerebral vessels by treating the vessels with GW3965 for 72 h to stimulate native apoE secretion from astrocytes and perfusing HDL through the lumen just after Aβ injection. More specifically, tripartite vessels were treated with the LXR agonist GW3965 (0.8 µM) for 72 h to stimulate astrocyte apoE3 secretion. Aβ40 and Aβ42 monomers (1 µM) were injected in the tissue chamber in the absence or presence of 200 µg/ml of circulating HDL, with or without GW3965. The levels of transported Aβ was measured by ELISA from samples collected from the lumenal circulating medium at the indicated times over 4 h (FIGS. 5A-B), and from vascular tissue collected 24 h after Aβ injection (FIGS. 5C-D). Aβ transport (FIGS. 5F-G) and tissue accumulation (FIGS. 5H-I) were directly compared between bipartite and tripartite bioengineered vessels as above. Graphs represent mean±SEM for at least four independent experiments. * p=0.05,  p=0.01 and * p=0.001.

Figure 1B:
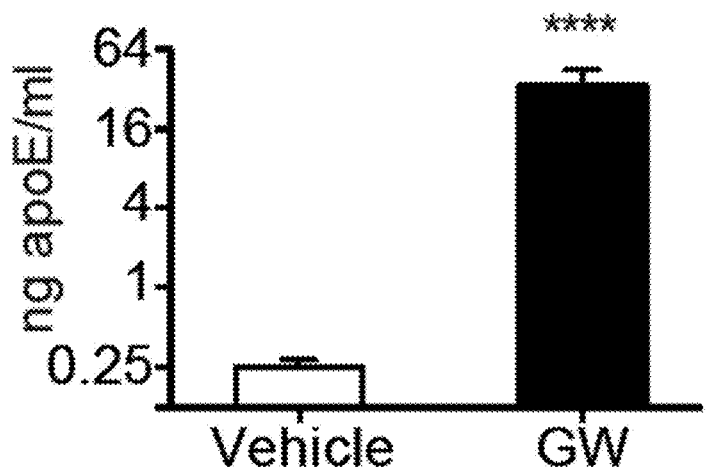
FIG. 1B is a bar graph showing astrocyte function, as confirmed by treating tissues with the Liver X Receptor (LXR) agonist GW3965 (GW) for 72 h and measuring the levels of astrocyte-derived apoE secreted into the tissue chamber. The graph represents mean±SEM for at least 4 independent experiments. * p=0.05,  p=0.01 and * p=0.001.
Figure 5A:
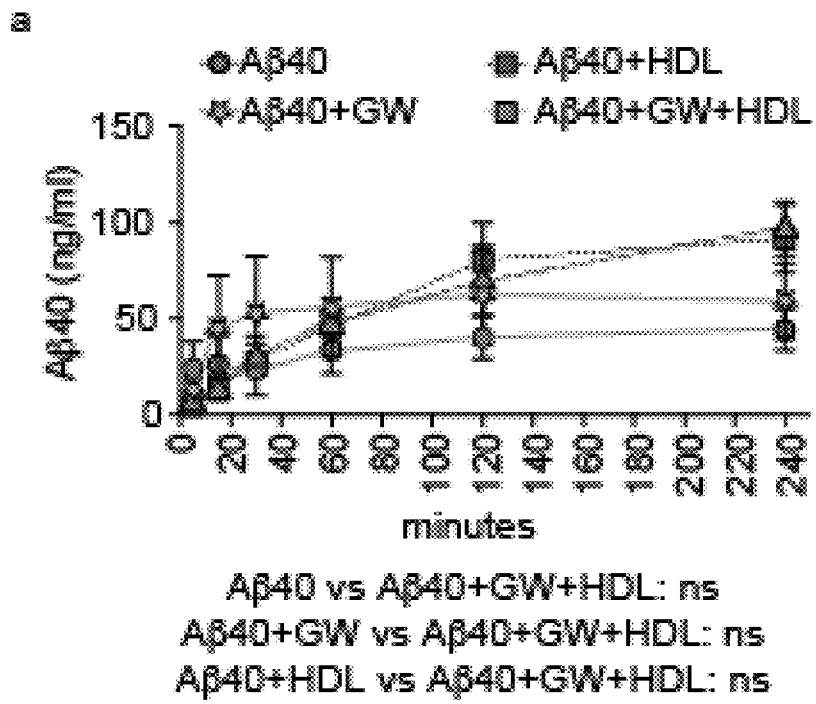
FIG. 5A is a line graph showing the effect of circulating HDL and the LXR agonist GW3965 on Aβ40 transport into luminal circulating medium in tripartite vessels using ELISA.
Figure 5B:
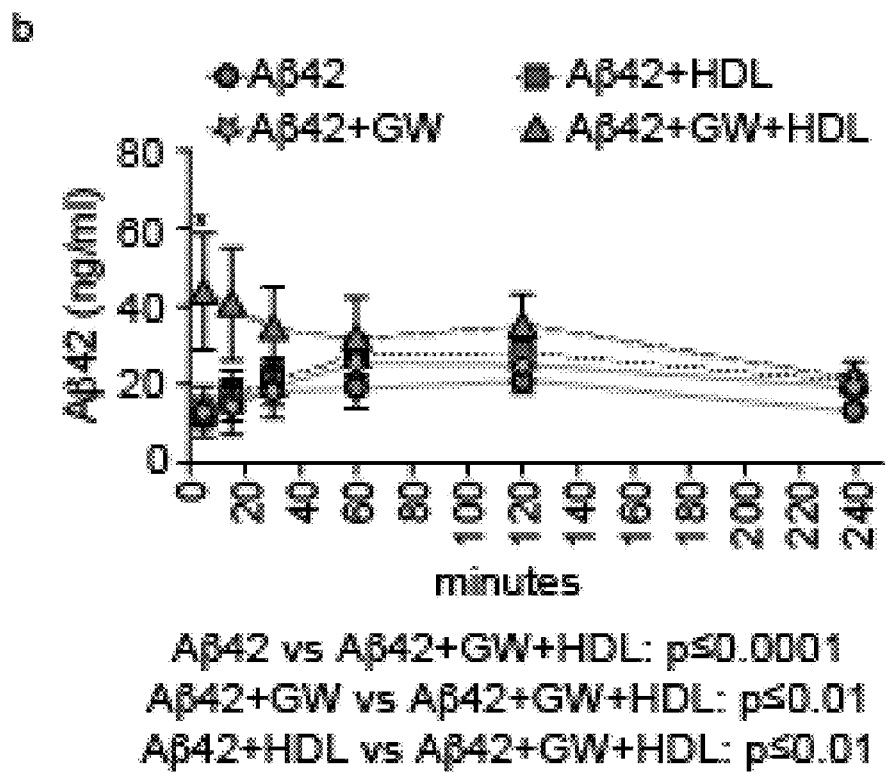
FIG. 5B is a line graph showing the effect of circulating HDL and the LXR agonist GW3965 on Aβ42 transport into luminal circulating medium in tripartite vessels using ELISA.
Figure 5C:
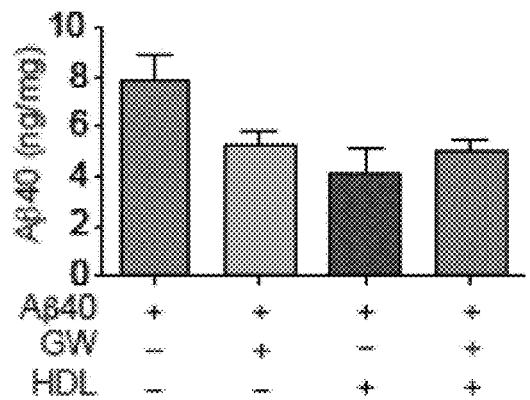
FIG. 5C is a bar graph showing the effect of circulating HDL and the LXR agonist GW3965 on Aβ40 accumulation in vascular tissue in tripartite vessels using ELISA.
Figure 5D:
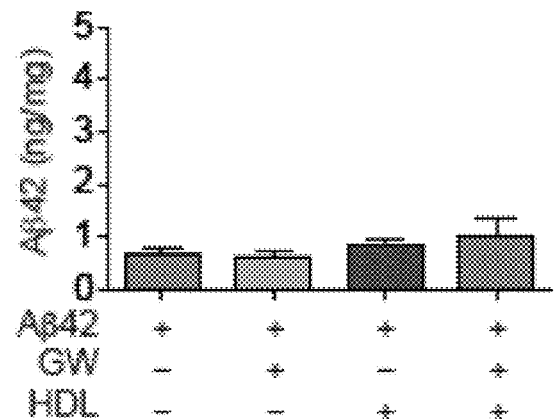
FIG. 5D is a bar graph showing the effect of circulating HDL and the LXR agonist GW3965 on Aβ42 accumulation in vascular tissue in tripartite vessels using ELISA.
Figure 5E:
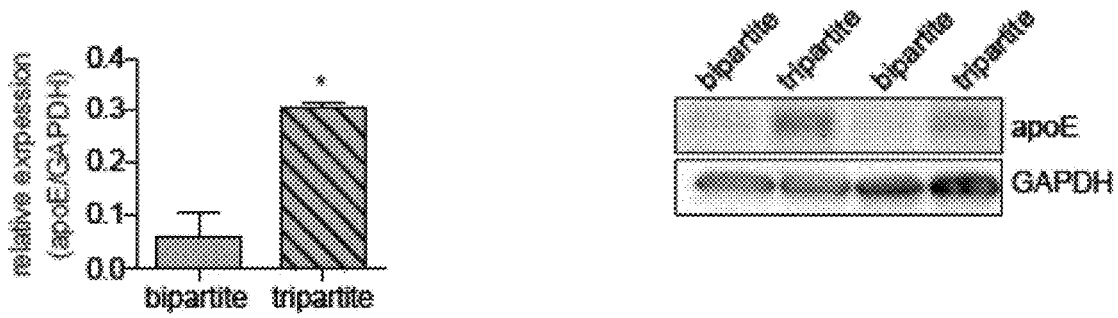
FIG. 5E is a bar graph (left panel) and photograph (right panel) showing the quantification of apoE in bipartite and tripartite vessels using western blotting.
Figure 5F:
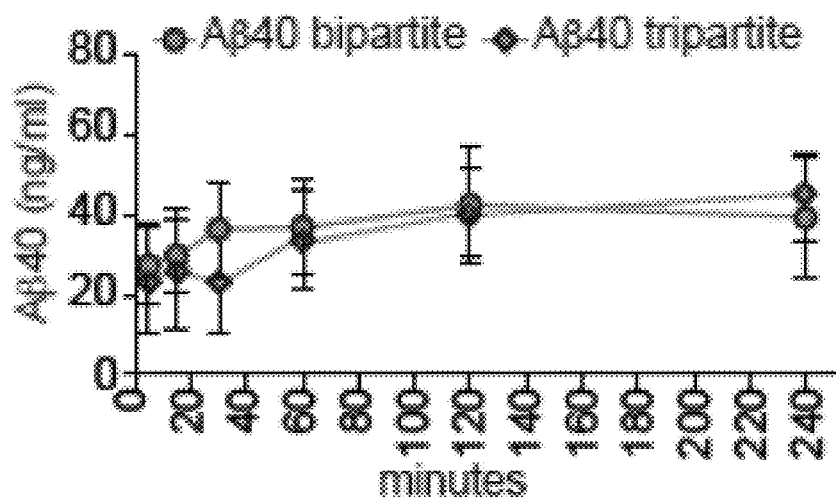
FIG. 5F is a line graph comparing the effect of bipartite and tripartite vessels on Aβ40 transport into luminal circulating medium using ELISA.
Figure 5G:
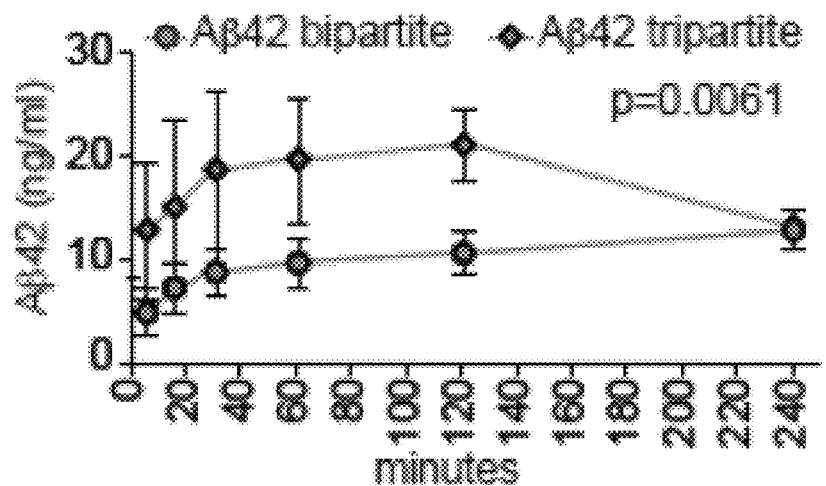
FIG. 5G is a line graph comparing the effect of bipartite and tripartite vessels on Aβ42 transport into luminal circulating medium using ELISA.
Figure 5H:
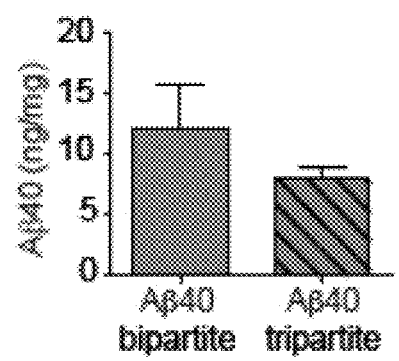
FIG. 5H is a bar graph showing comparing the effect of bipartite and tripartite vessels on Aβ40 accumulation in vascular tissue using ELISA.
Figure 5I:
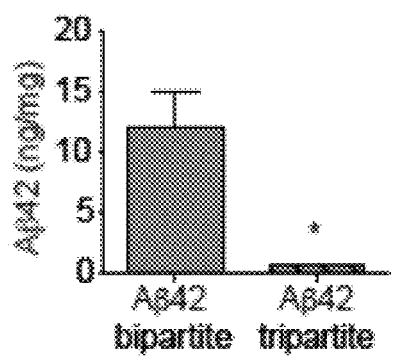
FIG. 5I is a bar graph comparing the effect of bipartite and tripartite vessels on Aβ42 accumulation in vascular tissue using ELISA.

Consistent with our observations in bipartite vessels, neither apoE alone nor HDL alone modified the rate of Aβ40 or Aβ42 transport through tripartite vessels over 4 h (FIGS. 5A-B). However, the combination of apoE and HDL together resulted in a significantly increased initial rate of Aβ42 transport without affecting Aβ40 (FIGS. 5A-B). Interestingly, relative to baseline tripartite conditions, neither apoE, HDL, nor both apoE and HDL affected accumulation of Aβ40 or Aβ42 within tripartite tissues after 24 h (FIGS. 5C-D), which differs from our observations in bipartite vessels (FIGS. 3A-H and 4A-H). To further understand the discrepancy between bipartite and tripartite vessels for Aβ42 tissue accumulation, we hypothesized that basal levels of native apoE secreted from astrocytes in tripartite vessels might reduce Aβ accumulation. Western blotting was used to confirm that tripartite tissue lysates had significantly more apoE than bipartite tissue under baseline conditions (FIG. 5E). We then directly compared Aβ transport and tissue accumulation between bipartite and tripartite vessels and observed increased Aβ42 but not Aβ40 recovery into circulation medium in tripartite compared to bipartite vessels (FIGS. 5F-G). With respect to tissue accumulation, Aβ42 levels were significantly lower and Aβ40 levels showed a trend to lower levels tripartite compared to bipartite vessels (FIGS. 5H-1). Notably, Aβ42 levels in tripartite vessels was similar to those observed in bipartite vessels to which recombinant apoE2 was added (FIG. 4I, FIG. 5I).

Example 6—Aβ Monomers, Oligomers and Fibrils Accumulate in Bipartite and Tripartite Tissue Dose Dependently To further investigate whether Aβ isoforms might differentially accumulate in the vasculature dependently of astrocyte apoE we compared Aβ isoforms accumulation in tripartite compared to bipartite tissues dose dependently. More specifically, Aβ40 and Aβ42 monomers (FIGS. 6A-B), oligomers (FIGS. 6C-D) or fibrils (FIGS. 6E-F) (1 NM) were injected in the chamber of bipartite and tripartite tissues. Aβ40 and Aβ42 at the indicated dose were injected in the tissue chamber and maintained 48 h under flow condition. The levels of vascular Aβ were measured by ELISA from samples collected 24 h after Aβ injection (FIGS. 6A-F). Graphs represent mean±SEM for at least 2 independent experiments.

Aβ40 and Aβ42 monomers accumulated dose dependently in both bipartite and tripartite tissues, however, tripartite tissue accumulations were lower for all doses (FIGS. 6A-B). Aβ40 and Aβ42 oligomers accumulated dose dependently in both bipartite and tripartite tissues, interestingly, tripartite tissue accumulations were similar between bipartite and tripartite (FIGS. 6C-D). Aβ40 and Aβ42 fibrils accumulated dose dependently in both tissue types with no difference between bipartite and tripartite tissues (FIGS. 6E-F). Taken all together these results strongly suggest that astrocyte apoE might prevent Aβ accumulation by maintaining Aβ solubility.

These results support a functional cooperation between apoE and circulating HDL to promote clearance of Aβ42 through the cerebral vessel by mechanisms that remain to be fully elucidated. That HDL and apoE consistently affected Aβ42 more than Aβ40 suggests that Aβ40 may be less amenable to lipoprotein-mediated transit across and removal from the vascular wall compared to Aβ42. These data are consistent with the observation that Aβ40 is the predominant species found in CAA. These results are also consistent with the hypothesized effects of apoE isoform on vascular function, as it is demonstrated that recombinant apoE2 promotes more Aβ42 clearance than recombinant apoE4. Importantly, the bioengineered blood vessel platform provides an opportunity to evaluate potential therapeutic strategies to facilitate Aβ clearance, including approaches that target HDL or apoE.

Figure 7A:
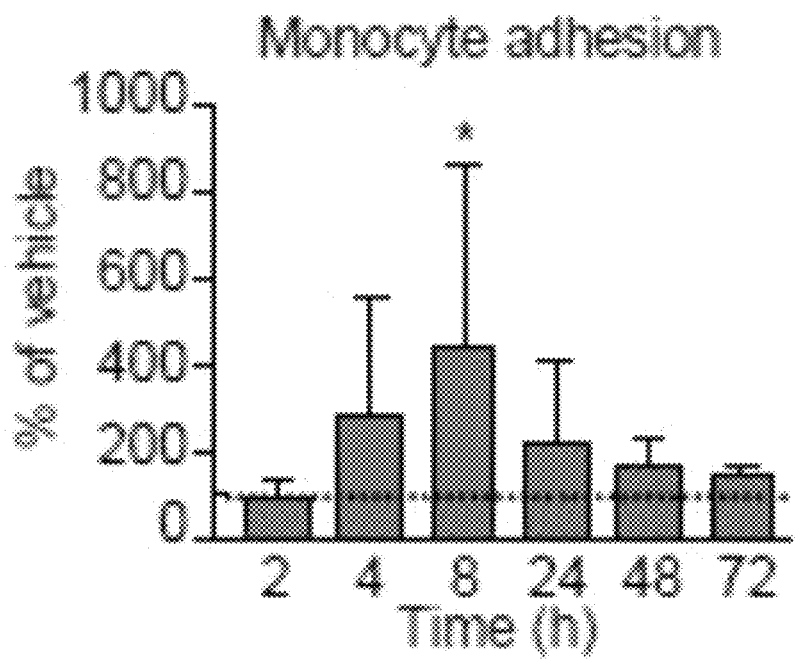
FIG. 7A is a bar graph showing the effect of Aβ40 on monocyte adhesion.
Figure 7B:
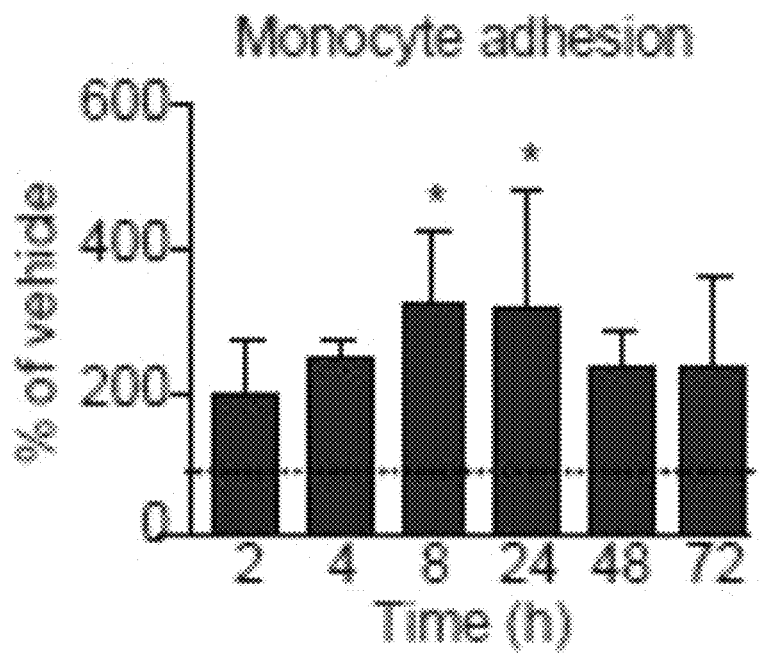
FIG. 7B is a bar graph showing the effect of Aβ42 on monocyte adhesion.
Figure 7C:
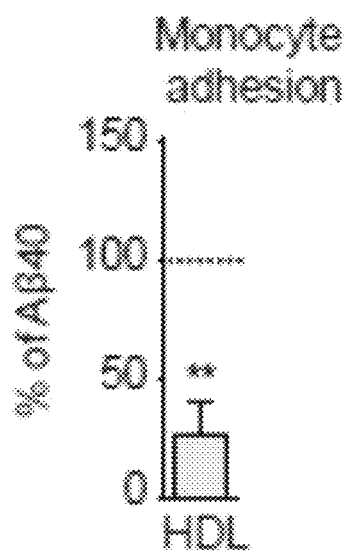
FIG. 7C is a bar graph showing the effect of HDL on Aβ40-induced EC activation.
Figure 7D:
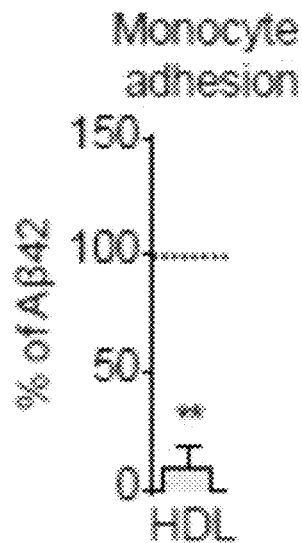
FIG. 7D is a bar graph showing the effect of HDL on Aβ42-induced EC activation.
Figure 7E:
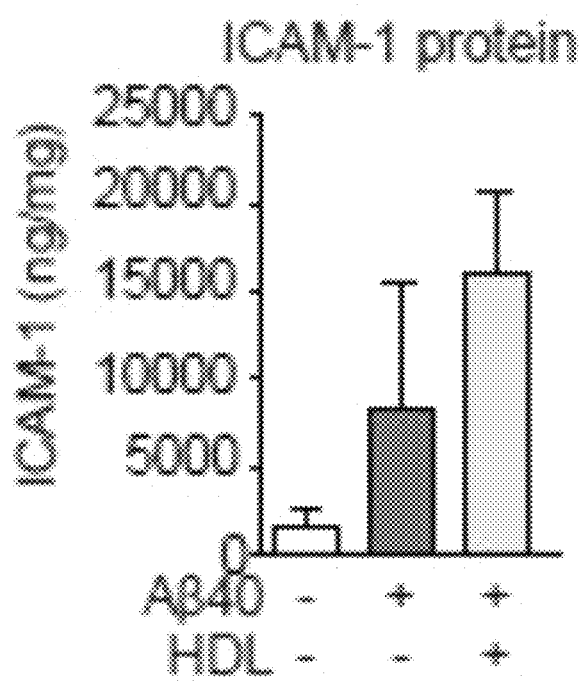
FIG. 7E is a bar graph showing the effect of HDL on Aβ40-induced ICAM-1 expression.
Figure 7F:
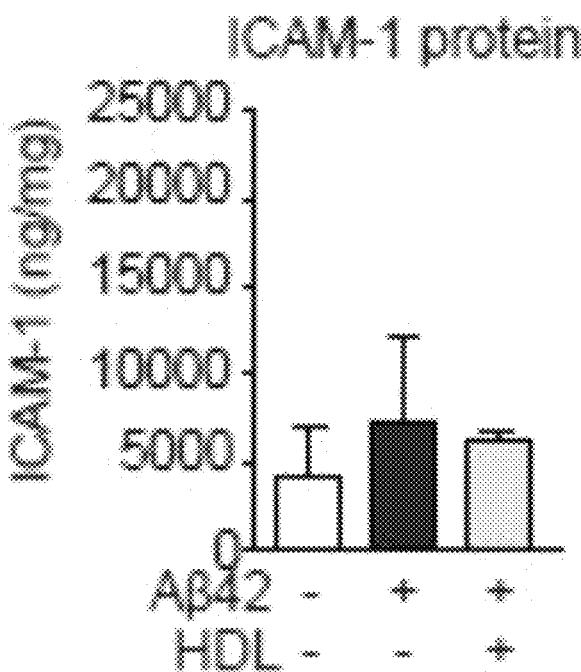
FIG. 7F is a bar graph showing the effect of HDL on Aβ42-induced ICAM-1 expression.

Example 7—HDL Suppresses Aβ-Mediated Monocyte Adhesion in Three-Dimensional Dynamic Engineered Human Vessels Because static monotypic cell cultures do not reflect the complexity of the native vascular environment, we enhanced the physiological relevance of our studies using vessels engineered from primary human EC and human smooth muscle cells (hSMC) in a flow bioreactor. We first confirmed that HDL can suppress Aβ-mediated activation in HUVEC cells, as the flow conditions used to generate engineered vessels are optimal using HUVECs but thus far incompatible with hCMEC/D3. HUVEC are therefore a suitable proxy to investigate Aβ and HDL effects in 3D engineered vessels. 1 µM Aβ40 or Aβ42 was injected directly into the graft chamber to mimic Aβ coming from the brain anteluminal side, followed by injection of human THP1 cells into the lumen chamber to mimic circulating monocytes. Both Aβ40 and Aβ42 led to endothelial activation in the engineered vessels as measured by monocyte adhesion, with the most robust response appearing 8 h after Aβ injection (FIG. 7A-B). We then tested the ability of HDL to suppress Aβ-induced EC activation in engineered vessels by circulating either media alone or 200 µg/ml of HDL for 2 h prior to injecting 1 µM Aβ into the graft chamber. In this novel engineered vascular model, HDL robustly suppressed endothelial activation by both Aβ40 (5 fold, p=0.0286) and Aβ42 (10 fold, p=0.0016) (FIG. 7C-D) without reducing ICAM-1 expression (FIG. 7E-F). As shown in these examples, the bioengineered vessels mimic a native vessel with a luminal monolayer of human ECs surrounded by several layers of human SMCs, through which human mononuclear cells can be circulated under flow conditions. Here, we injected Aβ on the anteluminal side to mimic brain-produced Aβ and circulated HDL and monocytes through the lumen. We confirmed that Aβ induces monocyte adhesion to ECs under native-like flow conditions in engineered human vessels, which can be suppressed by HDL independent of changes in ICAM-1 levels.

Example 8—Impact of Plasma from Healthy or Type II Diabetic Donors on the Transport and Accumulation of Aβ

Smooth muscle cells (SMC) and endothelial cells (EC) were sequentially seeded into tubular PGA/PCL scaffolds and grown under native-like pulsatile flow conditions. After 4 weeks in culture, Aβ42 are injected within the tissue chamber (antelumen) in the absence or presence of either luminal HDL (200 µg/ml), plasma from a healthy donor (ratio 25% plasma:75% endothelial medium) (labelled as healthy donor) or plasma from a T2DM (labelled as T2DM donor) (ratio 25% plasma:75% endothelial medium).

Figure 8A:
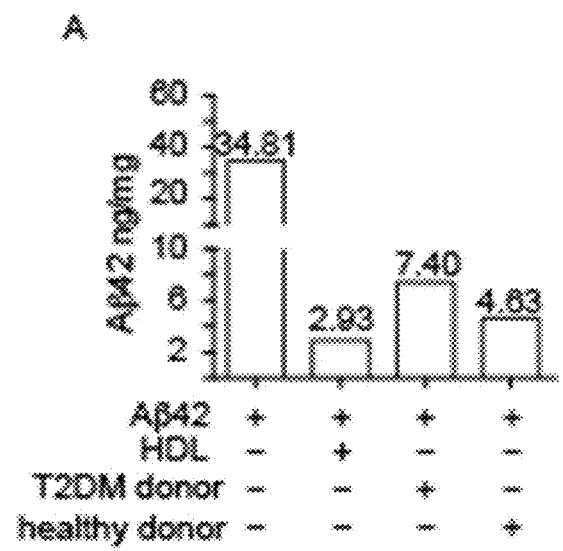
FIG. 8A is a bar graph showing the quantification of Aβ in vessel tissue after 24 hr using ELISA, where HDL from a healthy donor, or plasma from a type II diabetes mellitus donor, or plasma from a healthy donor has been circulated through the vessel lumen.
Figure 8B:
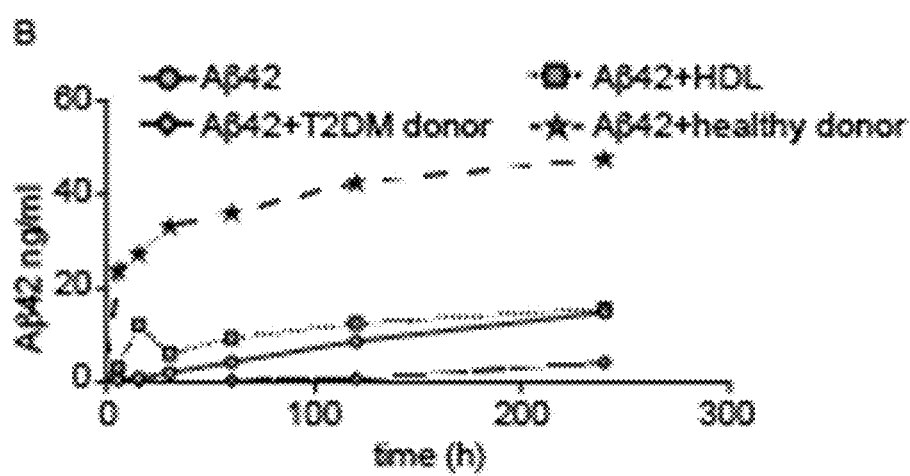
FIG. 8B is a bar graph showing the levels of transported Aβ as measured by ELISA in the luminal circulating medium at the indicated times over a 4 h hour period, where HDL from a healthy donor, or plasma from a type II diabetes mellitus donor, or plasma from a healthy donor has been circulated through the vessel lumen.

As shown in FIGS. 8A-C, when plasma (n=1) of a diagnosed T2DM patient (HbA1C % 6.7) was circulated through the lumen of our bipartite vessel for 24 h, Aβ42 accumulation was reduced compared to Aβ42 alone but to a lower extent compared to healthy plasma (FIG. 8A). Aβ42 transport in the first 4 h following Aβ42 injection was strongly enhanced when healthy plasma was circulated but T2DM plasma failed to increase Aβ42 transport (FIG. 8B). Similarly, monocyte binding was reduced in the case of the healthy donor but the T2DM donor failed to alter monocyte binding compared to Aβ42 alone (FIG. 8C). HDL was used as a known reducer of Aβ42 accumulation and monocyte binding. Thus, plasma from healthy or a T2DM patient have differential effects on HDL-mediated Aβ transport and accumulation in bipartite vessels. Taken together, these data demonstrate the capacity of our model to circulate unfractionated patient-derived plasma through our vascular model and strongly suggests the capacity to discriminate across patient groups using whole plasma obtained from subjects with different pathologies, through the differential effects of unfractionated plasma on vascular pathology.

Example 9—Structural and Functional Characterisation of Quadripartite Bioengineered Cerebral Vessels To extend the translational relevance of bioengineered vessels, we incorporated human IPSC-derived neurons on the antelumen. As the diameter of the vessels is approximately 2 mm prior to cell seeding and further contains muscular cells, our bioengineered quadripartite vessels were designed to resemble larger human penetrating arteries rather than the microvasculature.

Smooth muscle (SMC) and endothelial cells (EC) were sequentially seeded onto tubular scaffolds in the presence of astrocytes (Ast) and neurons (N) and grown under native-like pulsatile flow condition. After 4 weeks in culture, engineered vessels were immunostained against α-smooth muscle actin (SMC marker), CD31 (EC marker), GFAP (Ast marker) and β-tub III and MAP2 (neuron markers). Co-staining for GFAP and MAP2 confirms close proximity of neurons and astrocytes. Co-staining for Synapsin and MAP2 confirms the formation of synapses between neurons.

Quadripartite vascular tissues were composed of EC lining the lumen, several layers of SMC, several layers of astrocytes and neurons in the antelumen as confirmed by immunofluorescent staining against CD31, α-SMC actin, GFAP, and MAP2 respectively. Interestingly co-immunostaining for GFAP and MAP2 demonstrated an interlaced network of astrocyte and neurons whereas co-immunostaining of MAP2 and synapsin demonstrated the formation of synapses.

Figure 9B:
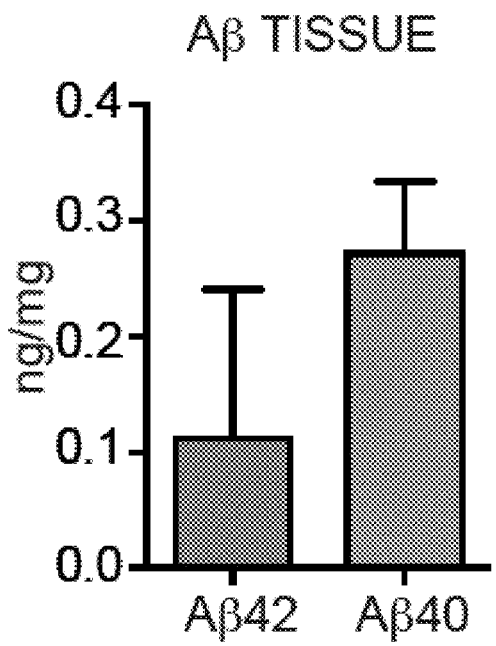
FIG. 9B is a bar graph showing the level of Aβ as measured by ELISA in the quadripartite tissues.
Figure 9C:
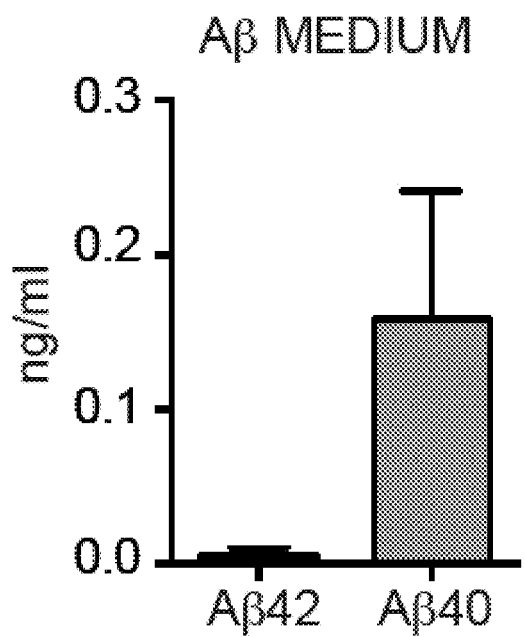
FIG. 9C is a bar graph showing the level of Aβ as measured by ELISA in the circulating medium of quadripartite tissues.

The functionality of the neurons was further evaluated by measuring glutamate release in the absence and presence of 50 nM of KCL for 30 min. Glutamate release was then measured by HPLC (FIG. 9A). The increased glutamate release after KCl incubation confirmed the functionality of the neuron and their cortical differentiation. Finally, the secretion of endogenous neuronally-produced Aβ40 and Aβ42 in quadripartite tissue (FIG. 9B) and in circulatory medium (FIG. 9C) as measured by commercial ELISA as above. These data confirmed that our quadripartite bioengineered tissue has both structural and functional characteristics of native cerebral cortical arteries.

All citations are hereby incorporated by reference.

The present invention has been described with regard to one or more embodiments. However, it will be apparent to persons skilled in the art that a number of variations and modifications can be made without departing from the scope of the invention as defined in the claims.

What is claimed is:

1. A method of determining the risk for a cerebrovascular dysfunction in a subject in need thereof comprising:
   i) providing a synthetic blood vessel;
   ii) providing an Aβ peptide;
   iii) contacting the synthetic blood vessel with a sample from the subject; and
   iv) determining the level of Aβ deposition or transport in the sample, wherein the subject has an increased risk for a cerebrovascular dysfunction if the level of Aβ deposition is increased or if Aβ transport is reduced.

2. The method of claim 1 further comprising monitoring the risk for the cerebrovascular dysfunction.

3. The method of claim 1 wherein the sample comprises HDL or apoE or a combination thereof.

4. The method of claim 2 further comprising providing a monocyte cell and determining the level of monocyte adhesion.

5. The method of claim 3 further comprising determining the level of endothelial cell activation.

6. The method of claim 1 wherein the cerebrovascular dysfunction is type II diabetes mellitus, hypercholesterolemia, hypertension, cerebral amyloid angiopathy (CAA), ischemic brain injury, stroke, dementia, cognitive impairment and Alzheimer's disease.

7. The method of claim 1 wherein the subject is a human.

* * * * *